(12) United States Patent
Thill

(10) Patent No.: US 6,632,610 B2
(45) Date of Patent: Oct. 14, 2003

(54) METHODS OF IDENTIFICATION AND ISOLATION OF POLYNUCLEOTIDES CONTAINING NUCLEIC ACID DIFFERENCES

(75) Inventor: Gilbert Thill, Bois Colombes (FR)

(73) Assignee: Gensat S.A. (FR)

( * ) Notice: Subject to any disclaimer, the term of this patent is extended or adjusted under 35 U.S.C. 154(b) by 42 days.

(21) Appl. No.: 09/882,608

(22) Filed: Jun. 15, 2001

(65) Prior Publication Data

US 2002/0055109 A1 May 9, 2002

Related U.S. Application Data

(60) Provisional application No. 60/240,262, filed on Oct. 12, 2000.

(51) Int. Cl.[7] .................................................. C12Q 1/68
(52) U.S. Cl. ........................................ 435/6; 435/91.2
(58) Field of Search .................................... 435/6, 91.2

(56) References Cited

U.S. PATENT DOCUMENTS

| | | | |
|---|---|---|---|
| 5,449,603 A | 9/1995 | Nielson et al. | |
| 5,811,239 A | 9/1998 | Frayne | |
| 6,027,877 A | 2/2000 | Wagner, Jr. | |
| 6,033,861 A | 3/2000 | Schafer et al. | |
| 6,251,590 B1 | 6/2001 | Schweighoffer et al. | |

FOREIGN PATENT DOCUMENTS

| | | | |
|---|---|---|---|
| WO | WO 97/21800 | 6/1997 | |
| WO | WO-974555 A1 * | 12/1997 | |
| WO | WO 99/36575 A1 | 7/1999 | |
| WO | WO 99/46403 A1 | 9/1999 | |

OTHER PUBLICATIONS

Stanley F. Nelson, et al.; "Genomic Mismatch Scanning: a New Approach to Genetic Linkage Mapping"; Nature Genetics, May 1993; pp. 11–17; vol. 4.

Paul Davis, et al.; "An Evaluation of Methods for the Purification of DNA Preparations"; J. Lab. Clin. Med.; Oct. 1981, pp. 549–557; vol. 98, No. 4; The C. V. Mosby Co.

Patrick C. Swanson, et al.; "Ligand Recognition by Anti–DNA Autoantibodies, Affinity, Specificity, and Mode of Binding"; Biochemistry 1996, vol. 35, pp. 1624–1633; American Chemical Society.

Ralph R. Meyer, et al.; "The Single–Stranded DNA–Binding Protein of *Escherichia coli*"; Microbiological Reviews; Dec. 1990, pp. 342–380; American Society for Microbiology.

John W. Chase, et al.; "Single–Stranded DNA Binding Proteins Required for DNA Replication"; Ann. Rev. Biochem,; 1986; vol. 55, pp. 103–136; Annual Reviews, Inc.

Ellis, L.A., et al., "MutS binding Protects Heteroduplex DNA from Exonuclease Digestion in vitro: a simple method for detecting mutations", *Nucl. Acids Res.* (1994), 22(13):2710–2711; XP–000606262; Oxford University Press.

Wagner, R., et al., "Mutation detection using immobilized mismatch binding protein (MutS)", *Nucl. Acids Res.* (1995), 23(19):3944–3948; XP–002030020; Oxford University Press.

* cited by examiner

*Primary Examiner*—Jeffrey Fredman
*Assistant Examiner*—Juliet Einsmann Switzer
(74) *Attorney, Agent, or Firm*—Saliwanchik, Lloyd & Saliwanchik

(57) ABSTRACT

The present invention is directed to methods of isolation of related polynucleotides harboring nucleic acid difference within a polynucleotide sample. The method will be useful in detecting and identifying alternative splicing events and corresponding splicing isoforms and to detect genomic DNA differences between genomes. The method according to the present invention is based on the use of a single-stranded trap. The single-stranded trap preferably involves the use of single-strand binding protein.

23 Claims, 9 Drawing Sheets

|     | A | B |
|-----|---|---|
| I1  | + | + |
| I2  | + | − |
| I3  | − | + |
| I4  | − | − |

| Combinations of 4 isoforms | Identification of A and B |
|---|---|
| I1/ I2 | − |
| I1/ I3 | − |
| I1/ I4 | + |
| I2/ I3 | + |
| I2/ I4 | − |
| I3/ I4 | − |
| I1/I2/I3 | + |
| I1/I2/I4 | + |
| I1/I3/I4 | + |
| I2/I3/I4 | + |
| I1/I2/I3/I4 | + |
| 11 combinations | 7 combinations |

FIGURE 6

```
                    SEQUENCE LISTING

<160> NUMBER OF SEQ ID NOS: 3

<210> SEQ ID NO 1
<211> LENGTH: 24
<212> TYPE: DNA
<213> ORGANISM: Artificial sequence
<220> FEATURE:
<223> OTHER INFORMATION: Sequence source:/note="synthetic construct"

<400> SEQUENCE: 1
cccgccacgt ccaagcggcc gcag                                          24

<210> SEQ ID NO 2
<211> LENGTH: 22
<212> TYPE: DNA
<213> ORGANISM: Artificial sequence
<220> FEATURE:
<223> OTHER INFORMATION: Sequence source:/note="synthetic construct"

<400> SEQUENCE: 2
ctgcggccgc ttggacgtgg cg                                            22

<210> SEQ ID NO 3
<211> LENGTH: 18
<212> TYPE: DNA
<213> ORGANISM: Artificial sequence
<220> FEATURE:
<223> OTHER INFORMATION: Sequence source:/note="synthetic construct"

<400> SEQUENCE: 3
acgtccaagc ggccgcag                                                 18
```

METHODS OF IDENTIFICATION AND ISOLATION OF POLYNUCLEOTIDES CONTAINING NUCLEIC ACID DIFFERENCES

FIELD OF THE INVENTION

The present invention relates to the field of biotechnology and describes methods of identification and cloning of nucleic acid differences between polynucleotides from different sources, origins, environments or different physiological situations.

BACKGROUND OF THE INVENTION

The nucleotide sequence of a given gene may be different between individuals within a single species, between cells within a single individual, between both chromosomes within the same cell. Such differences may result from genetic variation or environmental change in DNA by insertions, deletions, point mutations, or by acquiring foreign DNA or RNA by means of infection by bacteria, molds, fungi and viruses. For example, acquisition by pathogens of a sudden resistance to a given drug may be caused by the deletion or to an acquisition of a new sequence in the genome. Alternatively, pathogenesis may result from insertion or deletions of genomic regions. For instance, the fragile X syndrome, the most common cause of inherited mental retardation, is partly due to an insertion of multiple CGG trinucleotides in the 5' untranslated region of the fragile X mRNA resulting in the inhibition of protein synthesis via ribosome stalling (Feng et al., *Science* 268:731–4, 1995). Alterations in nucleotide sequences can have profound effects on cells. For example, many tumors and many genetic diseases result from alteration, or mutation, of particular nucleotide sequences. Mutations in nucleotide sequences that encode proteins can result in production of proteins with altered polypeptide sequences and, in some instances, altered biological activities. Changes in the activity of a single protein can sometimes have profound effects on the physiology of an entire organism.

In order to develop effective preventive, diagnostic and therapeutic methods for treatment of cancer and hereditary diseases, we must first identify the genetic mutations that contribute to disease development. Typically, mutations are identified in studies of cloned genes whose normal sequences are already known (see, for example, Suzanne et al., Science 244:217, 1989; Kerem et al., Science 245:1073, 1989). That is, a gene is first identified as being associated with a disorder, and particular sequence changes that correlate with the diseased state are subsequently identified.

In addition to variations on genomic DNA, variation of nucleotide sequence may also occur between the different messenger RNA molecules transcribed from a single gene. Indeed, the pre-mRNAs of some genes may be spliced in various ways to produce different mRNAs, thus leading to the synthesis of protein isoforms that may exhibit different functions. Such alternative splicing may depend on the cell type, the stage of development, or the chemical or physical environment of the cell. Alternative splicing of pre-mRNAs is a powerful and versatile regulatory mechanism that can affect quantitative control of gene expression and lead to functional diversification of proteins.

The prevalence of alternative splicing as a mechanism for regulation of gene expression makes it a very likely target for alterations leading to human disease. The splicing machinery can be altered in several circumstances. For example, a gene mutation can disturb the splicing profile by inactivating physiological splicing sites or uncovering cryptic splicing sites. More particularly, genetic point mutations could alter or eliminate the splice junctions and prevent normal splicing yielding either aberrantly truncated transcripts or transcripts containing an exon which is normally deleted and/or missing another exon which is normally present.

Multiple examples of splicing alterations are associated with diseases or related disorders. Indeed, 15% of the gene mutations associated with diseases alter the process of RNA splicing. Many cancer-associated genes are alternatively spliced and their expression leads to the production of multiple splice variants (Mercatante and Kole, Pharmacol Ther 2000, 85:237–43). Although the functions of most of these variants are not well-defined, some have antagonistic activities related to regulated cell death mechanisms. In a number of cancers and cancer cell lines, the ratio of splice variants is frequently shifted so that the anti-apoptotic splice variant predominates. Therefore, characterization of these splice variants can lead to the identification of new therapeutic targets and the design of new drugs and new means of diagnosis.

A variety of techniques have been used to identify sequence variations in nucleic acids. For example, Restriction Fragment Length Polymorphism (RFLP) analysis detects restriction sites generated by mutations or alterations in nucleotide sequences (see Kan et al., Lancet ii:910, 1978); Denaturing Gradient Gel Electrophoresis and Single Stranded DNA Electrophoretic Mobility Studies identify nucleotide sequence differences through alterations in the mobility of bands in electrophoresis gels (see Myers et al., Nature 313:495, 1985; Orita et al., Proc. Natl. Acad. Sci. USA 86:2766, 1989); Chemical Cleavage analysis identifies mismatched sites in heteroduplex DNA (see Cotton, Proc. Natl. Acad. Sci. USA 85:4397, 1988); and RNase Cleavage analysis identifies mismatched sites in RNA-DNA or RNA-RNA heteroduplexes (see Myers et al., Science 230:1242, 1985; Maniatis et al. U.S. Pat. No. 4,946,773).

A significant problem with each of the above-described methods for identifying nucleic acid sequence differences is that prior knowledge of the gene of interest is generally required.

Three methods have been recently developed to detect and eventually subsequently identify nucleic acid differences without prior knowledge of the gene presenting such difference. These methods rely on the fact that complementary strands of related polynucleotides will be able to anneal to each other forming double stranded molecules except for the nucleic acid difference, thus forming heteroduplexes. If the difference consists in a single nucleotide difference or a small insertion or deletion, a mismatched duplex is formed. If the difference comprises a large nucleotide region, a duplex with an internal single stranded region is formed.

The WO 99/36575 patent application, which disclosure is hereby incorporated by reference in its entirety, discloses methods in which mismatched duplex nucleic acid molecules formed from hybridization within two source populations of nucleic acids are isolated from the rest of the sample using an enzyme able to bind to the mismatched duplex, such as MutS. However, this technique does not apply to heteroduplexes containing internal single stranded regions larger than mismatched regions of a few nucleotides.

The U.S. Pat. No. 5,922,535 patent, which disclosure is hereby incorporated by reference in its entirety, discloses a method in which nucleic acid strands from different populations are hybridized with one another so that heteroduplexes are formed. Then, those heteroduplexes are cleaved in a heteroduplex-dependent fashion and cleavage products are isolated and used to identify the genetic sequence that differ in the nucleic acid populations. The WO 99/46043 patent application, which disclosure is hereby incorporated by reference in its entirety, discloses methods in which internal loops of heteroduplexes are retrieved by digestion of double stranded regions of such heteroduplexes. However, these last two methods does not allow to isolate directly full-length polynucleotides containing nucleic acid differences but only fragments thereof.

The present invention discloses methods to isolate related polynucleotides harboring nucleic acid differences, or fragment thereof, including regions surrounding said nucleic acid differences, wherein said nucleic acid difference consists in insertions or deletions, or replacement of large regions of nucleotides. Such methods are particularly interesting to isolate genomic insertions/or deletions, alternative splicing events and sequence extension repeats.

One of the advantage of these techniques is to isolate not only the nucleic acid differences but also the flanking sequences and even the full length polynucleotides harboring said nucleic acids differences. Such full-length polynucleotide are then available for several applications, for example for cloning and/or sequencing.

SUMMARY OF THE INVENTION

The invention relates to methods of isolation of related polynucleotides harboring nucleic acid differences in a polynucleotide sample, said method comprising the selection of heteroduplexes containing at least one internal single stranded region (herein referred to as ISSRHs) with a single stranded trap (herein referred to as SST), wherein said ISSRHs are formed between said related polynucleotides and wherein said internal single stranded regions represent said nucleic acid differences.

In an embodiment of the present invention, said single-stranded trap involves the use of a Recognition Element (RE) having a preferential affinity for single-stranded polynucleotides compared to double stranded polynucleotides. In a preferred embodiment of the present invention, said single-stranded trap involves the use of a Recognition Element (RE) having a preferential affinity for single-stranded DNA compared to double stranded DNA. In a more preferred embodiment, said RE has a preferential affinity for DNA compared to RNA. In a further preferred embodiment, said RE has a preferential affinity for single stranded DNA compared to double stranded DNA and to single stranded RNA under conditions used to select single stranded DNA.

In another preferred embodiment, said RE is an antibody. In another preferred embodiment, said RE is a peptide. In still another preferred embodiment, said RE is a protein. Even more preferably, said RE is a single strand binding protein (SSB). Even more preferably, said RE is selected from the group consisting of the *E. coli.* SSB, the product of gene 32 of phage T4, the adenovirus DBP and the calf thymus UP1. Even more preferably, said RE is the *E. coli.* SSB. In still another preferred embodiment, said RE is a material selected from the group consisting of benzoylated-naphthoylated-DEAE-cellulose (BNDC), methylated albumin on bentonite (MAB) and methylated albumin on Kieselgur (MAK). More preferably, said RE is BNDC.

In one embodiment, said polynucleotide sample contains single-stranded polynucleotides. Preferably, said single stranded polynucleotides comprises both (+) strands and (−) strands. In another embodiment, said polynucleotide sample contains double-stranded polynucleotides. In an additional embodiment, said polynucleotide sample contains both single-stranded and double-stranded molecules.

In one embodiment, said polynucleotide sample contains DNA. In a preferred embodiment, said polynucleotide sample contains cDNA. In another preferred embodiment, said polynucleotide sample contains genomic DNA. In another embodiment, said polynucleotide sample contains RNA, preferably mRNA. In still another embodiment, said polynucleotide sample contains both DNA and RNA, preferably cDNA and mRNA.

In one embodiment, said polynucleotide sample comprises polynucleotides from a single source or a single environment or a single physiological condition. In another embodiment, said polynucleotide sample comprises a mixture of polynucleotides from samples coming from at least two different sources, environments or physiological conditions.

In one embodiment, said polynucleotide sample comprises polynucleotides derived from a single gene or limited set of genes. In a preferred embodiment, said polynucleotide sample comprises cDNA or mRNA derived from a single gene or limited set of genes. In another embodiment, the polynucleotide sample comprises a complex polynucleotide mixture. In a preferred embodiment, the polynucleotide mixture comprises a cDNA collection, an mRNA collection or both a cDNA and mRNA collection.

More particularly, the invention relates to a method of isolation of related polynucleotides harboring nucleic acid differences in a polynucleotide sample, said method comprising the following steps:

obtaining a polynucleotide sample containing said related polynucleotides;

annealing polynucleotides present in said sample to allow the formation of ISSRHs between said related polynucleotides; and selecting said ISSRHs using a single-stranded trap.

Optionally, said method comprises an additional step of reducing the size of polynucleotides, preferably by fragmentation, more preferably to a size suitable for single pass DNA sequencing. Preferably the reduction step is performed before step (c), more preferably before step (b).

Optionally, said method comprises an additional step of denaturing said polynucleotides in said sample before the annealing step (b).

Optionally, said method comprises an additional step of removing single-stranded regions other than internal single-stranded regions on ISSRHs, wherein said additional step occurs before step (c).

Optionally, said method comprises an additional step of blunting polynucleotides obtained after step (b), wherein said additional step preferably occurs before step (c), more preferably after the cleaning step.

Optionally, the method comprises an additional step of ligating an oligonucleotide adapter to polynucleotide ends. Preferably, said method comprises an additional step of ligating an oligonucleotide adapter to the ends of polynucleotides after step (b). More preferably, said ligation step is performed after said cleaning step, after said blunting step, or after said cleaning and blunting steps. Optionally, said method comprises an additional step of removing totally or partially adapters from the ends of polynucleotides, preferably after the amplification step, more preferably after the amplification step and before either the cloning step or another cycle of isolation of related polynucleotides containing nucleic acid differences.

Optionally, said method comprises an additional step of amplifying ISSRHs selected by said single stranded trap, preferably using polymerase chain reaction (PCR).

Optionally, said isolation method may be repeated several times, preferably 1, 2, 3 or 5 times.

Optionally, said isolation method comprises a final step of cloning said isolated polynucleotides.

Optionally, said isolation method comprises a final step of identifying said nucleic acid differences of said isolated polynucleotides, preferably using DNA sequencing.

In one embodiment, the invention concerns a method of isolation of related DNA molecules harboring nucleic acid differences in a DNA sample, said method comprising the following steps:

obtaining a DNA sample containing said related polynucleotides;
a) denaturating DNA molecules in said sample;
annealing said denatured DNA molecules to allow the formation of ISSRHs between said related DNA molecules; and
removing single stranded regions other than internal single stranded regions of ISSRHs;
b) selecting said ISSRHs using a single-stranded trap; and amplifying, using PCR, said ISSRHs selected by said single-stranded trap.

Optionally, said method comprises an additional step of reducing the size of DNA molecules, preferably by fragmentation, more preferably to a size suitable for single pass DNA sequencing. Preferably the reduction step is performed before step (e), more preferably before step (b). Optionally, said method comprises an additional step of blunting polynucleotides obtained after step (c) and before step (e).

In another embodiment, the invention concerns a method of isolation of related DNA molecules harboring nucleic acid differences in DNA sample, said method comprising the following steps:

obtaining a DNA sample containing said related DNA molecules;
a) denaturating DNA molecules in said sample;
annealing said denatured DNA molecules to allow the formation of ISSRHs between said related DNA molecules; and
removing single stranded regions other than internal single stranded regions of ISSRHs;
ligating adapters to the ends of said ISSRHs;
b) selecting said ISSRHs using a single-stranded trap; and
amplifying, using PCR, said ISSRHs selected by said single-stranded trap.

Optionally, said method comprises an additional step of reducing the size of DNA molecules, preferably by fragmentation, more preferably to a size suitable for single pass DNA sequencing. Preferably the reduction step is performed before step (f), more preferably before step (b). Optionally, said method comprises an additional step of blunting polynucleotides obtained after step (c) and before step (e). Optionally, said method comprises an additional step of removing said adapters totally or partially from the ends of said amplified ISSRHs.

In a preferred embodiment, selection of said ISSRHs in any of the methods of the invention comprises the following steps:

i) mixing said sample with said RE under condition to allow the binding of said internal single stranded regions within said ISSRHs to said RE and subsequent formation of internal single stranded region containing heteroduplex-recognition element (ISSRH-RE) complexes; and ii) separating said ISSRH-RE complexes from said sample. Alternatively, said single stranded trap comprises the following steps:

i) immobilizing said RE;

ii) bringing said immobilized RE into contact with said annealed sample to allow the binding of said internal single stranded regions within said ISSRH to said RE and subsequent formation of internal single stranded region containing heteroduplex-recognition element (ISSRH-RE) complexes; and iii) removing the unbound polynucleotides.

Optionally, any selection method of the invention may comprises the additional step of recovering said related polynucleotides from said ISSRH-RE complexes.

More particularly, the invention relates to a method to isolate polynucleotides subjected to alternative splicing, comprising the steps of:

a) obtaining a double stranded cDNA sample containing splicing isoforms;

b) denaturing said cDNA to obtain single stranded cDNA;

c) annealing said single stranded cDNAs under conditions allowing the formation of ISSRHs between single stranded cDNAs from different splicing isoforms, wherein an internal single stranded region comprises said alternative splicing event;

d) removing single stranded regions other than internal single stranded regions of said ISSRHs;

e) ligating an adapter to the ends of blunted cDNAs;

f) selecting said ISSRHs with a SST; and g) amplifying said selected cDNAs.

Optionally, said method comprises an additional step of blunting polynucleotides obtained after step (c) and before step (e). Optionally, said method comprises an additional step of reduction, wherein the size of polynucleotides is reduced, preferably by fragmentation. Preferably the reduction step is performed before step (c), more preferably before step (b).

In one embodiment, said cDNA sample comprises polynucleotides from a single source, a single environment or a single physiological condition. In another embodiment, said cDNA sample comprises a mixture of polynucleotides from samples coming from at least two different sources, environments or physiological conditions.

In one embodiment, said cDNA sample comprises cDNA derived from a single gene or limited set of genes. In another embodiment, the cDNA sample comprises a complex polynucleotide mixture. In a preferred embodiment, the cDNA mixture comprises a cDNA collection, an mRNA collection or both a cDNA and mRNA collection.

The invention encompasses ISSRH-REs obtainable by any method of the invention. The invention also encompasses ISSRH-REs obtained by any method of the invention.

The invention also encompasses libraries obtained using any of the methods of the invention. Preferably, said library is enriched in related polynucleotides harboring at least one nucleic acid difference. More preferably, said library is enriched in alternative splicing isoforms or alternative splicing events.

The invention encompasses any polynucleotides isolated, or fragments thereof, using any method of the invention. Preferably, said isolated polynucleotides are polynucleotides harboring a nucleic acid difference. In one embodiment, said isolated polynucleotides derive from the same gene by alternative splicing. In a preferred embodiment, said isolated polynucleotides differ by the presence of at least one exon or part of an exon in one polynucleotide compared to the other. In another preferred embodiment, said isolated polynucleotides differ by the replacement of one exon in one polynucleotide by a different exon in the other polynucleotide. In another embodiment, said isolated polynucleotides differ by the insertion, deletion or replacement of a nucleotide sequence on one gene compared to an allelic variant of the same gene.

The invention also encompasses polynucleotides able to hybridize, preferably specifically, to a polynucleotide isolated using any method of the invention, preferably under stringent conditions. Preferably said polynucleotides is able to hybridize, preferably specifically, to a nucleic acid difference isolated using any method of the invention, preferably under stringent conditions.

In one embodiment, said nucleic acid difference comprises an insertion, deletion, or replacement of at least 6, 8, 10, 12, 15, 18, 20, 25, 50, 75, 100, 150, 200, 300, 500, 1000, 1500, 2000, 3000, 5000, 10000 or 50000 nucleotides. Preferably, said nucleic acid difference comprises an insertion, deletion, or replacement of 10, 12, 15, 18, 20, 25, 50, 75, 100, 150, 200, 300, 500, 1000, 1500, 3000 or 5000 nucleotides. More preferably, said nucleic acid difference comprises an insertion, deletion, or replacement of 12, 15, 18, 20, 25, 50, 75, 100, 150, 200, 300, or 500 nucleotides. Even more preferably, said nucleic acid difference comprises an insertion, deletion, or replacement of 15, 18, 20, 25, 50, 75, 100, or 150 nucleotides.

The invention also encompasses all oligonucleotides, preferably primers and probes, that may be designed to detect a nucleic acid difference using a polynucleotides isolated by any method of the invention.

BRIEF DESCRIPTION OF THE DRAWINGS

In FIG. 2a, related polynucleotides differ by the addition/deletion of a region (shaded box). In FIG. 2b, related polynucleotides differ by the replacement of a region by another one (stripped boxes).

FIG. 6 illustrates the analysis of alternative splicing events using methods for identifying alternative splicing events for a single gene or limited set of genes comprising a reduction step. Two alternative splicing events (A and B) lead to 4 possible isoforms (I1, I2, I3, I4) and 7 combinations of these 4 isoforms out of 11 possible combinations in the initial sample lead to the identification of these two ASEs. For more detail, see Example 3, section "ASE identification".

DETAILED DESCRIPTION

Figure 1:
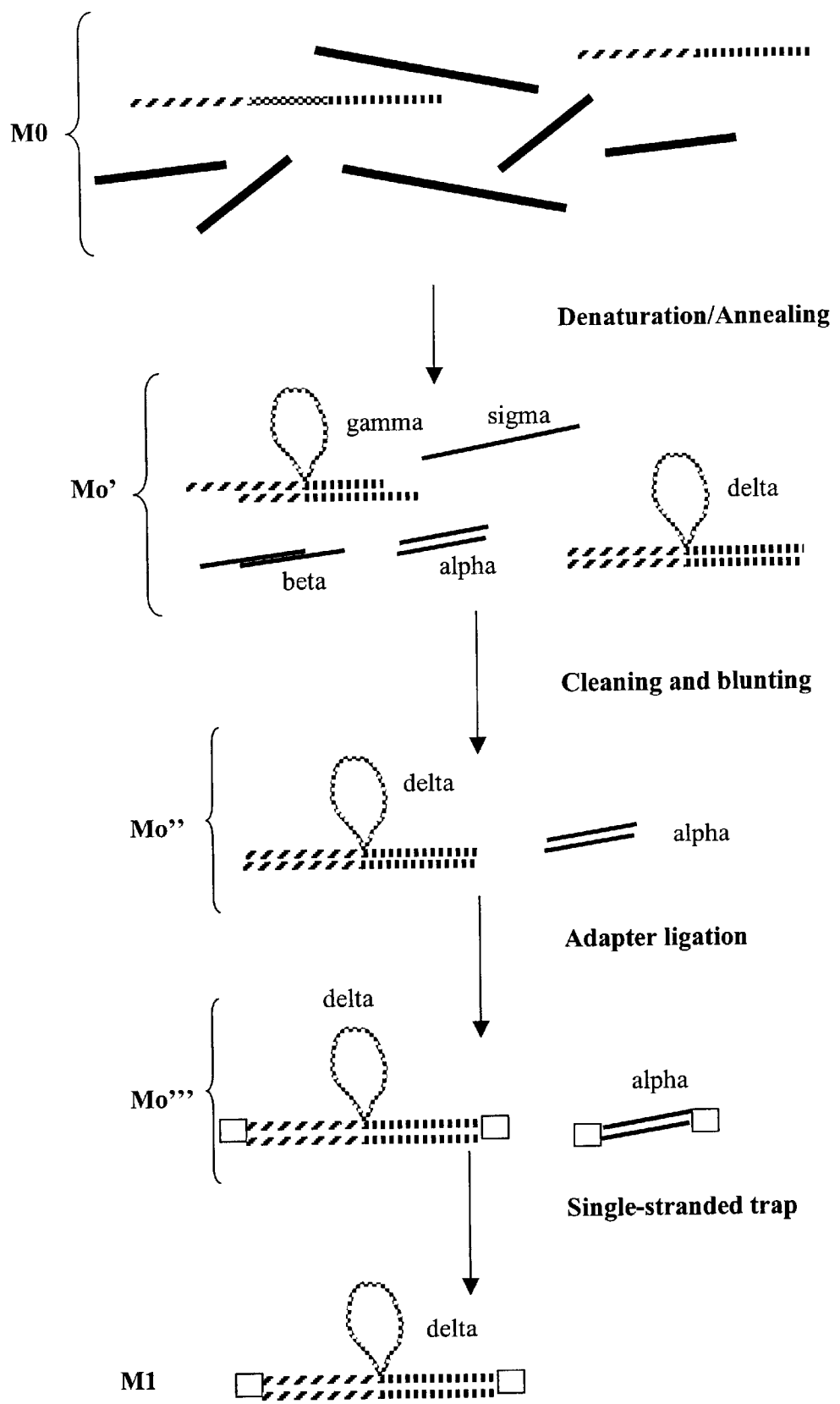
FIG. 1 illustrates several steps of the methods of the invention for the isolation of related polynucleotides harboring nucleic acid differences. The Mo sample comprises double-stranded polynucleotides represented by black thick lines. Two related polynucleotides harboring nucleic acid differences are represented by lines with hashed marks. The molecules alpha represent perfect or nearly perfect homoduplexes. The molecules beta represent duplexes with single-stranded tails. The molecules sigma represent single-stranded molecules. The molecules gamma represent heteroduplexes with an internal single-stranded region and with single-stranded tails. The molecules delta represent heteroduplexes with an internal single-stranded region and blunt ends. The white rectangles represent the adapters.

The invention describes methods for the isolation of related polynucleotides harboring nucleic acid differences in a polynucleotide sample. Such methods of isolating nucleic acid differences are characterized by the use of a single-stranded trap (SST) which is the core of the present invention.

More particularly, the invention relates to the isolation of related polynucleotides harboring nucleic acid differences in a polynucleotide sample, said methods comprising the step of selecting heteroduplexes containing internal single stranded regions (ISSRHs) with a single stranded trap (SST), wherein said heteroduplexes are formed between said related polynucleotides and wherein said single stranded regions represent said nucleic acid differences. In a preferred embodiment of the invention, said SST involves the use of a Recognition Element (RE) having a preferential affinity for single-stranded polynucleotides compared to double stranded polynucleotides. Preferably, said RE is a protein or a peptide characterized by a preferential affinity to single-stranded DNA compared to double-stranded DNA. More preferably, said RE is a protein or a peptide characterized by a specific affinity to single-stranded DNA. Even more preferably, said RE is selected from the group consisting of the *E. coli.* SSB, the product of gene 32 of phage T4, the adenovirus DBP and the calf thymus UP1. Even more preferably, said RE is the *E. coli.* SSB. In another preferred embodiment, said RE is an antibody, preferably an autoantibody. In still another preferred embodiment, said RE is a material selected from the group consisting of benzoylated-naphthoylated-DEAE-cellulose (BNDC), methylated albumin on bentonite (MAB) and methylated albumin on Kieselgur (MAK). More preferably, said RE is BNDC.

The first step is to obtain a sample containing the related polynucleotides of interest, said sample comprising either a targeted nucleic acid population or complex nucleic acid population. Next, the polynucleotides in said polynucleotide sample are annealed to form duplexes. A single-stranded trap is then used to purify the heteroduplexes having one or several internal single-stranded regions, whereby the internal single-stranded regions correspond to nucleic acid differences between said related polynucleotides that have annealed to form said heteroduplexes.

Therefore, the invention encompasses methods of isolation of related polynucleotides harboring nucleic acid differences in a polynucleotide sample, said methods comprising the following steps:

obtaining a sample containing said related polynucleotides;

annealing polynucleotides present in said sample to allow the formation of heteroduplexes containing internal single stranded regions (ISSRHs) between said related polynucleotides; and selecting said ISSRHs with a single-stranded trap.

Optionally, said method comprises an additional step of reducing the size of polynucleotides, preferably by fragmentation, more preferably to a size suitable for single pass DNA sequencing. Preferably the reduction step is performed before step (c), more preferably before step (b).

Optionally, said method comprises an additional step of denaturing said polynucleotides in said sample before the annealing step (b) in cases where said sample contain double stranded polynucleotides.

Optionally, said method comprises an additional step of removing single-stranded regions other than internal single-stranded regions on ISSRHs, wherein said additional step occurs after step (b) and before step (c). This additional step is referred to as the cleaning step.

Optionally, said method comprises an additional step of blunting polynucleotides obtained after step (b), wherein said additional step preferably occurs before step (c), more preferably after the cleaning step.

Optionally, the method comprises an additional step of ligating an oligonucleotide adapter to polynucleotides to allow subsequent cloning and/or subsequent amplification. Said adapter ligation may be performed at any convenient step of the method. For example, said adapter ligation is carried out after said annealing step or after said blunting step Preferably, said ligation step is performed after said cleaning and blunting steps. Alternatively, said ligation step is performed after the selecting step with the SST. Optionally, ligated adapters are cleaved from polynucleotides at any convenient step of the method, preferably after the amplification step and before either the cloning step or another cycle of enrichment for polynucleotides containing nucleic acid differences. The cleavage of said adapters is an optional step for cloning of polynucleotides of interest.

Optionally, said method comprises an additional step of amplifying ISSRHs selected by said single stranded trap, preferably using polymerase chain reaction (PCR).

Optionally, said isolation method, or enrichment cycle consisting in the annealing and selection steps, and optionally of the reduction, denaturation, cleaning, blunting, adapter ligation, adapter removal and PCR amplification steps may be repeated several times, preferably 1 to 5 times.

Optionally, said isolation method comprises a final step of cloning said isolated polynucleotides.

Optionally, said isolation method comprises a final step of identifying said nucleic acid differences of said isolated polynucleotides, preferably using DNA sequencing.

Definitions

As used interchangeably herein, the terms "nucleic acid molecule(s)" and "polynucleotide(s)" include RNA or DNA (either single or double stranded, coding, complementary or antisense), or RNA/DNA hybrid sequences of more than one nucleotide in either single chain or duplex form (although each of the above species may be particularly specified). In particular, it encompasses genomic DNA (gDNA), complementary DNA (cDNA), pre messenger RNA (pre-mRNA), incompletely spliced mRNA, and messenger RNA (mRNA). The term "nucleotide" is used herein as an adjective to describe molecules comprising RNA, DNA, or RNA/DNA hybrid sequences of any length in single-stranded or duplex form. More precisely, the expression "nucleotide sequence" encompasses the nucleic material itself and is thus not restricted to the sequence information (i.e. the succession of letters chosen among the four base letters) that biochemically characterizes a specific DNA or RNA molecule. The term "nucleotide" is also used herein as a noun to refer to individual nucleotides or varieties of nucleotides, meaning a molecule, or individual unit in a larger nucleic acid molecule, comprising a purine or pyrimidine, a ribose or deoxyribose sugar moiety, and a phosphate group, or phosphodiester linkage in the case of nucleotides within an oligonucleotide or polynucleotide. The term "nucleotide" is also used herein to encompass "modified nucleotides" which comprise at least one modifications such as (a) an alternative linking group, (b) an analogous form of purine, (c) an analogous form of pyrimidine, or (d) an analogous sugar. For examples of analogous linking groups, purine, pyrimidines, and sugars see for example PCT publication No. WO 95/04064, which disclosure is hereby incorporated by reference in its entirety. Preferred modifications of the present invention include, but are not limited to, 5-fluorouracil, 5-bromouracil, 5-chlorouracil, 5-iodouracil, hypoxanthine, xantine, 4-acetylcytosine, 5-(carboxyhydroxylmethyl)uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v) ybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid, 5-methyl-2-thiouracil, 3-(3-amino-3-N-2-carboxypropyl)uracil, and 2,6-diaminopurine. The polynucleotide sequences of the invention may be prepared by any known method, including synthetic, recombinant, ex vivo generation, or a combination thereof, as well as utilizing any purification methods known in the art. Methylenemethylimino linked oligonucleosides as well as mixed backbone compounds having, may be prepared as described in U.S. Pat. Nos. 5,378,825; 5,386,023; 5,489,677; 5,602,240; and 5,610,289, which disclosures are hereby incorporated by reference in their entireties. Formacetal and thioformacetal linked oligonucleosides may be prepared as described in U.S. Pat. Nos. 5,264,562 and 5,264,564, which disclosures are hereby incorporated by reference in their entireties. Ethylene oxide linked oligonucleosides may be prepared as described in U.S. Pat. No. 5,223,618, which disclosure is hereby incorporated by reference in its entirety. Phosphinate oligonucleotides may be prepared as described in U.S. Pat. No. 5,508,270, which disclosure is hereby incorporated by reference in its entirety. Alkyl phosphonate oligonucleotides may be prepared as described in U.S. Pat. No. 4,469,863, which disclosure is hereby incorporated by reference in its entirety. 3'-Deoxy-3'-methylene phosphonate oligonucleotides may be prepared as described in U.S. Pat. Nos. 5,610,289 or 5,625,050 which disclosures are hereby incorporated by reference in their entireties. Phosphoramidite oligonucleotides may be prepared as described in U.S. Pat. No. 5,256,775 or U.S. Pat. No. 5,366,878 which disclosures are hereby incorporated by reference in their entireties. Alkylphosphonothioate oligonucleotides may be prepared as described in published PCT applications WO 94/17093 and WO 94/02499 which disclosures are hereby incorporated by reference in their entireties. 3'-Deoxy-3'-amino phosphoramidate oligonucleotides may be prepared as described in U.S. Pat. No. 5,476,925, which disclosure is hereby incorporated by reference in its entirety. Phosphotriester oligonucleotides may be prepared as described in U.S. Pat. No. 5,023,243, which disclosure is hereby incorporated by reference in its entirety. Boranophosphate oligonucleotides may be prepared as described in U.S. Pat. Nos. 5,130,302 and 5,177,198 which disclosures are hereby incorporated by reference in their entireties.

The terms "complementary" or "complement thereof" are used herein to refer to the sequences of polynucleotides which is capable of forming Watson & Crick base pairing with another specified polynucleotide throughout the entirety of the complementary region. Watson & Crick base pairing refer to nucleotides which can be hydrogen bonded to one another be virtue of their sequence identities in a manner like that found in double-helical DNA with thymine or uracil residues linked to adenine residues by two hydrogen bonds and cytosine and guanine residues linked by three hydrogen bonds. For the purpose of the present invention, a first polynucleotide is deemed to be complementary to a second polynucleotide when each base in the first polynucleotide is paired with its complementary base. Complementary bases are, generally, A and T (or A and U), or C and G. "Complement" is used herein as a synonym from "complementary polynucleotide", "complementary nucleic acid" and "complementary nucleotide sequence". These terms are applied to pairs of polynucleotides based solely upon their sequences and not any particular set of conditions under which the two polynucleotides would actually bind. Unless otherwise stated, all complementary polynucleotides are fully complementary on the whole length of the considered polynucleotide.

The term "isolated polynucleotide", as used herein, requires that the polynucleotide be removed from its original environment (e. g., the natural environment if it is naturally occurring). For example, a naturally-occurring polynucleotide present in a living animal is not isolated, but the same polynucleotide separated from some or all of the coexisting materials in the natural system is isolated. Such polynucleotide could be part of a vector and/or such polynucleotide could be part of a composition, and still be isolated in that the vector or composition is not part of its natural environment. Specifically excluded from the definition of "isolated polynucleotide" are: naturally-occurring chromosomes (such as chromosome spreads), artificial chromosome libraries, genomic libraries, and cDNA libraries that exist either as an in vitro nucleic acid preparation or as a transfected/transformed host cell preparation, wherein the host cells are either an in vitro heterogeneous preparation or plated as a heterogeneous population of single colonies. Also specifically excluded are the above libraries wherein a specified polynucleotide makes up less than 5% of the number of nucleic acid inserts in the vector molecules. Further specifically excluded are whole cell genomic DNA or whole cell RNA preparations (including said whole cell preparations which are mechanically sheared or enzymatically digested). Further specifically excluded are the above whole cell preparations as either an in vitro preparation or as a heterogeneous sample separated by electrophoresis (including blot transfers of the same) wherein the polynucleotide of interest has not further been separated from the heterologous polynucleotides in the electrophoresis medium (e.g., further separating by excising a single band from a heterogeneous band population in an agarose gel or nylon blot).

The terms "purify" or "enrich", as used interchangeably herein, does not require absolute purity or enrichment; rather, they are intended as a relative definition. Purification of polynucleotides containing nucleic acid differences using the SST to at least one order of magnitude, preferably two or three orders, and more preferably four or five orders of magnitude is expressly contemplated. As an example, purification from 0.1% concentration to 10% concentration is two orders of magnitude. The term "purified" is further used herein to describe a polynucleotide which has been separated from other compounds including, but not limited to, polypeptides or polynucleotides, carbohydrates, lipids, etc. The term "purified" may also be used to specify the separation of covalently closed polynucleotides from linear polynucleotides. A polynucleotide is substantially pure when at least about 50%, preferably 60 to 75% of a sample exhibits a single polynucleotide sequence and conformation (linear versus covalently close). A substantially pure polynucleotide typically comprises about 50%, preferably 60 to 90% weight/weight of a polynucleotide sample, respectively, more usually about 95%, and preferably is over about 99% pure. Polynucleotide purity, or homogeneity, is indicated by a number of means well known in the art, such as agarose or polyacrylamide gel electrophoresis of a sample, followed by visualizing a single band upon staining the gel. For certain purposes higher resolution can be provided by using HPLC or other means well known in the art. As an alternative embodiment, purification of the polynucleotides may be expressed as "at least" a percent purity relative to heterologous polynucleotides (DNA, RNA or both). As a preferred embodiment, the polynucleotides are at least; 10%, 20%, 30%, 40%, 50%, 60%, 70%, 80%, 90%, 95%, 96%, 96%, 98%, 99%, or 100% pure relative to heterologous polynucleotides, respectively. As a further preferred embodiment the polynucleotides have a purity ranging from any number, to the thousandth position, between 90% and 100% (e.g., a polynucleotide at least 99.995% pure) relative to heterologous polynucleotides, or as a weight/weight ratio relative to all compounds and molecules other than those existing in the carrier. Each number representing a percent purity, to the thousandth position, may be claimed as individual species of purity.

The term "cDNA", as used herein, refers to the complementary DNA synthesized from a complete mRNA template or a fragment thereof. For example, the term cDNA refers to the full-length cDNA synthesized from a given mRNA and to any EST derived from said mRNA.

The term "(+) strand" refers to a DNA or RNA strand which has a sequence similar to the mRNA of a given gene and the term "(−) strand" refers to a DNA or RNA strand which has a the opposite sense and a complementary sequence to a mRNA of interest.

The term "duplex" refers to a polynucleotide containing a double-stranded region. A perfect duplex or "homoduplex" contains fully complementary strands and is thus a fully double stranded molecule. The term "heteroduplex" refers to a double-stranded polynucleotide containing regions that are not completely complementary, thus having also single stranded regions that are located either at the polynucleotide ends or internally, thus forming internal single stranded regions or mismatches. Such heteroduplexes arise from the hybridization of a (+) single strand and of a (−) single strand derived from related polynucleotides harboring nucleic acid differences. The heteroduplexes containing at least one internal single stranded region are referred to herein as ISSRHs. If the nucleic acid difference consists in the addition or deletion of a region of one related polynucleotide compared to the other related polynucleotide, such internal single stranded regions are "internal single stranded loops". If the nucleic acid difference consists in the replacement of a region by another for one related polynucleotide compared to the other related polynucleotide, such internal single stranded regions are "internal single stranded bubbles".

The term "single-stranded trap", as used herein, refers to a means to select molecules containing at least one single stranded nucleic acid region from other materials contained in a sample, i.e. other polynucleotides not containing single stranded regions, polypeptides, carbohydrates, and lipids. Such molecules may be single stranded nucleic acid molecules or any molecule, irrespective of its chemical nature, containing at least one region that is a single stranded nucleic acid region, irrespective of the location of said single stranded region in said molecule.

The term "related polynucleotides", as used herein, refers to polynucleotides having identical sequences except for one or a small number of regions that either have a different sequence, or are deleted or added from one polynucleotide compared to the other. Typical related polynucleotides are splicing isoforms of a same gene, or a gene harboring a genomic deletion or addition compared to another allele of the same gene. Such related polynucleotides may be either full-length polynucleotides such as genomic DNA, mRNAs, full-length cDNAs, or fragments thereof.

The term "nucleic acid difference" refers to nucleotide differences between related polynucleotides consisting essentially in the insertion, deletion or replacement of a region. Specifically excluded from the invention are mismatches consisting in nucleotide differences of only a few base pairs.

The term "alternative splicing event", as used herein, designates any sequence variation existing between two polynucleotide arising from the same gene or the same pre-mRNA by alternative splicing. This term also refers to polynucleotides, including splicing isoforms or fragments thereof, comprising said sequence variation. Preferably, said sequence variation is characterized by an insertion or deletion of at least one exon or part of an exon. The term "alternative splicing events" encompasses the original alternative splicing events, the skipping of exon (Dietz et al. , *Science* 259, 680 (1993); Liu et al., *Nature Genet.* 16, 328–329 (1997); Nyström-Lahti et al. *Genes Chromosomes Cancer* 26: 372–375 (1999)), differential splicing due to the cellular environmental conditions (e.g. cell type or physical stimulus) or to a mutation leading to abnormalities of splicing (Siffert et al., *Nature Genetics* 18: 45–48 (1998)).

The Polynucleotide Sample

The term "polynucleotide sample", as used herein, refers to any sample containing a collection of polynucleotides comprising at least two different polynucleotide species, i.e., polynucleotides having sequences not totally identical. Said polynucleotide sample may contain DNA (genomic DNA or gDNA, or cDNA), RNA (mRNA, pre-mRNA, or partially spliced RNA) or a mixture of them. Said polynucleotide sample may contain single-stranded, double-stranded molecules or a mixture of single stranded and double stranded nucleic acid molecules, wherein each form is an embodiment of the invention. Preferably, said polynucleotide sample contains a mixture of (+) strands and (−) strands. Preferably, said polynucleotide sample contains only or mostly double-stranded polynucleotides. More preferably, said polynucleotide sample contains only or mostly double stranded cDNAs, although single-stranded cDNA are also contemplated by the invention.

In one embodiment, the polynucleotide sample comprises a polynucleotide collection from a single source, a single environment or a single physiological condition . All sources, all physiological and environmental conditions one skilled in the art could envision are within the scope of the present invention. Preferably, said given physiological condition may be selected from the group consisting of healthy, pathologic, apoptotic, differentiated, undifferentiated conditions.

In another embodiment, said polynucleotide sample comprises a mixture of polynucleotides from samples coming from at least two different sources, environments or physiological conditions. Such different physiological or environmental conditions include but are not limited to control vs experimental, healthy vs infected, sensitive to X vs resistant to X, undifferentiated vs differentiated, normal vs transformed cells.

Said polynucleotide sample originating from a biological sample or from a cDNA or gDNA library will herein be referred to as a "complex polynucleotide sample". As used herein, the term "a complex polynucleotide sample" refers to a polynucleotide collection derived from an indefinite number of genes, some of which, are unknown. Alternatively, said polynucleotide sample containing a fairly limited number of polynucleotide species will herein be referred to as a "targeted polynucleotide sample". Such targeted polynucleotide sample contains polynucleotides derived from a single gene or from a limited set of genes. As used herein, the term "limited set of genes" refers to polynucleotides derived from a finite number of known genes, preferably at least 2, 3, 5, 10, 50, 100 or 500 defined genes.

In one embodiment, said polynucleotide sample comprises polynucleotides derived from a targeted polynucleotide sample. In another embodiment, said polynucleotide sample comprises polynucleotides derived from a complex polynucleotide sample. In still another embodiment, said polynucleotide sample comprises both polynucleotides derived from a targeted polynucleotide sample and polynucleotides derived from a complex polynucleotide sample. In still another embodiment, said polynucleotide sample comprises polynucleotides derived from complex polynucleotide samples that are mixed together.

A preferred polynucleotide sample for identifying alternative splicing events is a polynucleotide sample consisting in a double-stranded cDNA collection or in at least two double-stranded cDNA collections which are mixed. In another embodiment for identifying alternative splicing events, the polynucleotide sample contains a single-stranded cDNA collection or at least two single-stranded cDNA collections which are mixed. Preferably, said single-stranded cDNA collection(s) comprise(s) (+) single strands and (−) single strands. In a preferred embodiment for identifying alternative splicing events in a polynucleotide sample, a unique polynucleotide species for the gene of interest is mixed with a cDNA collection. Said unique polynucleotide species is added in excess, i.e. in a range of ratios of 1.01:1 to 100:1, preferably from 1.1:1 to 10:1, more preferably from 1.5:1 to 6:1 compared to the cDNA collection. Such resulting polynucleotide sample may be useful to identify more efficiently all splicing events existing for the gene(s) of interest within the cDNA collection.

A preferred polynucleotide sample for identifying genomic differences is a polynucleotide sample contains a double-stranded gDNA collection or at least two double-stranded gDNA collections which are mixed. In another embodiment, the polynucleotide sample contains a single-stranded gDNA collection or at least two single-stranded gDNA collections which are mixed. Preferably, said single-stranded gDNA collection(s) comprise(s) (+) single strands and (−) single strands.

The Biological Sample

The invention encompasses all biological samples containing polynucleotides without any particular limitation. More particularly, a biological sample according to the invention may originate from a cell, a tissue, an organ, a surgical or a biopsy specimen fixed or non-fixed such as bone marrow aspirates, or a biological fluid including body fluids such as whole blood, serum, plasma, cerebrospinal fluid, urine, lymph fluids, and various external secretions of the respiratory, intestinal and genitourinary tracts, tears, saliva, milk, white blood cells, and cell culture supernatants. The origin of the sample can be animal (preferably mammal, more preferably human), plant, virus, bacteria, protozoan or fungus. The sample may be eukaryotic, prokaryotic, or acellular. Cells comprised in the biological sample, especially when coming from a tissue, organ, biological fluid or biopsy, can be cultivated in order to increase the number of available cells. The sample may contain cells from a single type or of mixed cell type. The cells, tissues and specimens may originate from normal individuals or from patient suffering from a disease or a disorder. The disease or disorder can be, for example, a cancer, a neurodegenerative disease, an inflammatory disease, a cardiovascular disease, an immune disorder, a body weight disorder such as obesity, etc. Any particular cell, cell type, pathological cell, cell at a particular state of development or disease progression, are contemplated in the present invention.

Preparation of Complex Polynucleotide Samples

Preparation of complex polynucleotide samples are particularly suitable to systematically isolate all nucleic acid differences existing within a whole population of polynucleotides representative of genes expressed in a given context (intra sample difference). For example, a complex cDNA sample may be used to isolate all splicing events or all splicing isoforms existing in a given context for a whole biological sample. Preparation of complex polynucleotide samples are also suitable to subsequently isolate all nucleic acid differences existing between 2 or more whole populations of polynucleotides representing 2 or more different contexts (inter sample difference). For example, such a complex cDNA sample resulting from the mixing of polynucleotides from 2 or more biological samples is useful to isolate alternative splicing events or isoforms resulting from differential expression between the different biological samples. Alternatively, such a complex gDNA sample resulting from the mixing of genomes of 2 or more bacterial strains is useful to isolate genomic differences between those bacterial strains.

Preparation of Genomic DNA Samples

They are well known to those skilled in the art and include techniques described in Gilman et al. "Current Protocols in Molecular Biology", Volume 1, Chapter 2 (Ausubel et al., eds, John Wiley & Sons, New York, N.Y., 1994), which disclosure is hereby incorporated by reference in its entirety.

Preparation of RNA Samples

The complex polynucleotide sample may be prepared from populations enriched in total RNAs or from populations enriched in mRNAs.

Methods of extraction of total RNA are well-known in the art and are described, for example, in Sambrook et al., (1989) Molecular Cloning: A Laboratory Manual. 2ed. Cold Spring Harbor Laboratory, Cold Spring Harbor, N.Y., vol. 1, ch. 7; in "Current Protocols in Molecular Biology", supra, Chapter 4, in Chomczynski and Sacchi, (1987) *Anal. Biochem.* 162:156–159, the disclosures of which are incorporated herein by reference in their entireties. Typically, total RNA isolation is performed in the presence of chaotropic agents such as guanidinium chloride or guanidinium thiocyanate, followed by RNA extraction using solvents such as phenol, chloroform or a sample of both, although other detergents and extraction agents can alternatively be used. Some commercial kits are also available for the extraction of the total RNAs, for example US73750 kit (Amersham) and Rneasy kit (Quiagen).

Alternatively, the complex polynucleotide sample may be prepared from messenger RNAs. These mRNAs may be obtained either from commercial sources or from one of the numerous methods well known by the man skilled in the art. Messengers RNA can be isolated either directly from the biological sample or from total RNA extracts, using any method known to those skilled in the art including for example the use of polyT oligonucleotides (Aviv and Leder, *Proc. Natl. Acad. Sci. USA* 69:1408–1412, 1972), which disclosure is hereby incorporated by reference in its entirety. Typically, the mRNA is isolated from the total RNA by chromatography over oligo(dT)-cellulose or other chromatographic media that have the capacity to bind to the polyadenylated 3'-portion of mRNA molecules. Some commercial kits are also available to prepare mRNAs, for example Pharmacia Biotech, Piscataway N.J., 1995 catalog #27-9255-01 and #27-9254-01; Stratagene, La Jolla, Calif. 1995 catalog #200347, #200345, #200348,#200349, #200344, US72700 kit (Amersham) or oligo-dT beads kit (Dynal). Preferably, mRNAs are prepared from cytosolic total RNA in order to avoid contamination by pre-mRNAs or incompletely spliced pre-mRNA. This can be done with the Rneasy kit (N°74103, Quiagen). Commercially and/or publicly available mRNA libraries can also be used according to the present invention. For example, LABIMO and CLON- TECH sell total human RNAs or polyA+ RNAs derived from different tissues.

Preparation of cDNA Samples

In preferred embodiments of the invention, complex polynucleotide samples of the invention contain cDNA molecules prepared from total RNAs or from messenger RNAs using any one of the numerous methods well known in the art.

Generally, these methods involve the use of a reverse transcriptase for the synthesis of a single stranded cDNA from a mRNA template and an oligonucleotide primer. Experimental details can be found, for example, in "Current Protocols in Molecular Biology", supra, volume 1, chapter 5, and in Sambrook et al., supra, volume 2, chapter 8, which are enclosed herein by reference.

A number of reverse transcriptases have been described in the literature and are commercially available. For example, the most used ones are the AMV and MMLV virus reverse transcriptases. Furthermore, some thermostable DNA polymerases with reverse transcriptase activity from *Thermus flavus* and *Thermus thermophilus* HB-8 (Promega) may also be used. In a preferred embodiment, reverse transcriptases able to synthesize the first cDNA strand at a fairly high temperature, such as the AMV reverse transcriptase working around 42 degree Celsius and the Tth reverse transcriptase working up to 60 degree Celsius, are used in order to destabilize RNA secondary structures that could block elongation, therefore allowing to obtain longer cDNAs which will represent the initial mRNA population with an increased fidelity and efficiency. In another preferred embodiment, a reverse transcripase without any Rnase H activity is used in order to have a greater yield of cDNA synthesis and to prevent any RNA degradation during cDNA synthesis. Such Rnase H-reverse transcriptases may be prepared from any known enzyme having a reverse transcriptase activity by mutation or deletion. Alternatively, Such Rnase H-reverse transcriptases are commercially available (ref. 18053-017, Life Technologies).

Two kinds of oligonucleotide primers may be used to prepare the first cDNA strand, namely random or semi-random primers, and oligo dT primers. Random oligonucleotides are preferably 4 to 10 nucleotides in length, more preferably 6 nucleotides in length. This method is well known by the man skilled in the art and allows to initiate reverse transcription at different random positions of a RNA template. Alternatively, semi-random primers may be used, namely primers containing i) a stabilizing region that may contain internal primer sequences allowing further amplification and/or restriction sites to allow further cloning, ii) a random region and iii) a region of minimal priming allowing the primer to hybridize periodically. Further experimental detail may be found in WO 99/46403, which disclosure is hereby incorporated by reference in its entirety. In contrast to random or semi-random primers, oligo dT primers allow the initiation of the reverse transcription from the poly A tail of mRNAs. Preferably, the primer is 4 to 20 nucleotides in length, more preferably about 15 nucleotides in length. More preferably, the last 3' nucleotide of the oligo dT primer is degenerated to allows DNA synthesis to be initiated at the very beginning of the poly A tail.

Optionally, a labeled oligonucleotide primer may be used in order to identify, select or sort the template RNA from the neo-synthesized cDNA if necessary. Any labeling may be used by spectroscopic, photochemical, biochemical, immunochemical, or chemical means. For example, useful labels include radioactive substances (including, $^{32}P$, $^{35}S$, $^{3}H$, $^{125}I$), fluorescent dyes (including, 5-bromodesoxyuridin, fluorescein, acetylaminofluorene, digoxigenin) or biotin. Examples of non-radioactive labeling of oligonucleotides are described in the French patent No. FR-7810975 or by Urdea et al. (1988) or Sanchez-Pescador et al (1988), which disclosures are hereby incorporated by reference in their entireties. In addition, labeled oligonucleotides may have structural characteristics that allow signal amplification, such as branched DNA probes as described by Urdea et al. in 1991 or in the European patent No. EP 0 225 807 (Chiron), which disclosures are hereby incorporated by reference in their entireties.

Double stranded cDNAs are then synthesized from the obtained single stranded cDNA templates using any one of the methods known in the art including, for example, self-priming (see Sambrook et al., supra, pp 8.14,) and replacement synthesis (see Sambrook et al., supra, pp. 8.15; Klickstein et al. Current Protocols in Molecular Biology, supra, 1995, pp. 5.5.1–5.5.14, each of which is incorporated herein by reference). Preferred techniques use *E. coli* Rnase H, *E. coli* DNA polymerase I and *E. coli* DNA ligase. The final step of the second strand synthesis usually involves the use of the T4 DNA polymerase in order to obtain cDNA molecules with blunt ends.

Optionally, for best results in obtaining cDNAs which represent rare mRNAs, normalized cDNA libraries, namely libraries depleted in most of the abundant transcripts, may be prepared using any techniques known to those skilled in the art including those described in U.S. Pat. No. 5,637,685; Sankhavaram et al., (1991) Proc. Natl. Acad. Sci. USA 88, 1943–1947; Ko (1990), Nucl. Acids. Res. 18, 5709; and Bonaldo et al., Genome Res. 6: 791–806, which disclosures are hereby incorporated by reference in their entireties.

Preparation of Targeted Polynucleotide Sample

In this case, the polynucleotide sample does not contain the whole set of polynucleotides existing in a given biological sample or DNA library (i.e. complex polynucleotide sample) but it contains only a limited set of polynucleotides species obtained or derived from one gene or a limited set of genes.

Such targeted polynucleotide samples are particularly suitable to subsequently isolate all nucleic acid differences existing between polynucleotides deriving from a single gene or a limited set of genes and representative of a given environment or physiological situation. For example, a targeted cDNA sample may be used to study all alternative splicing events existing for a single gene or for a limited set of genes in a given context.

Such targeted polynucleotide samples are also suitable to subsequently isolate all nucleic acid differences existing between polynucleotides deriving from a single gene or a limited set of genes and representative of 2 or more different environment or physiological situations. For example, a targeted cDNA sample obtained by mixing polynucleotides from 2 or more different targeted cDNA samples representative of 2 or more different contexts is useful to isolate all splicing events representative of the differences among contexts for a single gene or a limited number of genes.

A targeted polynucleotide sample containing a limited number of polynucleotide species may be obtained from an initial complex polynucleotide sample using any methods known to those skilled in the art.

Any selection methods known to those skilled in the art may be used to select polynucleotides species of interest among a complex polynucleotide population. For example, as described in "Current Protocols in Molecular Biology", supra, Volume 1, Chapter 6, which disclosure is hereby incorporated by reference in its entirety, polynucleotides of interest may be detected and isolated by screening cDNA or gDNA libraries with hybridization probes able to bind specifically to the polynucleotides of interest derived from said single gene or said limited set of genes. Alternatively, target clones may be isolated using the RecA-based technology from CLONTECH Laboratories. RecA promotes formation of complexes between a single-stranded DNA probe and homologous double-stranded DNA molecules, thus allowing the direct isolation of double-stranded plasmids containing a target sequence. To perform the RecA-based selection procedure, all what is needed is sufficient sequence information from each target gene to design primers for amplification of a 200–300 bp, biotinylated probe. These PCR products are then denatured, complexed with RecA, and used for target clones selection within a given complex DNA library. [for more details, see the ClonCapture cDNA Selection Kit User Manual from Clontech (ref: PT3246-1), which disclosure is hereby incorporated by reference in its entirety]. An alternative to using the Clontech RecA-based technology would be to use the GeneTrapper technology from Gibco-BRL, which documentation is hereby incorporated by reference in its entirety.

Alternatively, double stranded cDNAs may be synthesized selectively from a RNA sample, preferentially a mRNA sample, using any methods known to those skilled in the art including those described in the section entitled "Preparation of cDNA samples" except that primers specific for the polynucleotides species of interest are used instead of non specific primers such as random, semi-random or oligo dT primers. Preferentially, such primers are designed in order to hybridize to the expected most 3' end of the transcribed portion of the gene(s) of interest in order to be able to synthesize cDNAs corresponding to as many splicing isoforms as possible. More preferentially, the primers are designed to be able to hybridize to the region containing the polyadenylation site in the last exon of the gene(s) of interest. Alternatively, the primers are designed to be able to hybridize to the last coding exon, preferably 3' to the stop codon for the protein(s) encoded by the gene(s) of interest. Optionally, several primers able to hybridize to different alternative most 3' exons may be designed for the same gene based either on experimental knowledge already accumulated concerning the existence of alternative 3' exons or on the prediction for alternative splicing using any software known by those skilled in the art.

Preferentially, methods of amplification are used to obtain targeted polynucleotide samples such as those disclosed elsewhere in the application. Any linear or logarithmic method of amplification may be used including the ligase chain reaction (LCR or Gap LCR) described in EP-A-320 308, WO 9320227 and EP-A-439 182, the polymerase chain reaction (PCR, RT-PCR) and techniques such as the nucleic acid sequence based amplification (NASBA) described in Guatelli et al., (1990) Proc. Natl. Acad. Sci. USA. 35:273–286 and in Compton (1991) Nature. 350(6313) :91–92, Q-beta amplification as described in European Patent Application No 4544610, strand displacement amplification as described in Walker et al., (1996) Clin. Chem. 42:9–13 and EP A 684 315 and target mediated amplification as described in PCT Publication WO 9322461, which disclosures are hereby incorporated by reference in their entireties. Alternatively, Asymmetric Gap LCR (RT-AGLCR) as described by Marshall et al., (1994) PCR Methods and Applications. 4:80-84, which disclosures are hereby incorporated by reference in their entireties, may be used to directly amplify RNA. The PCR technology is the most preferred amplification technique used in the present invention. A variety of PCR techniques are familiar to those skilled in the art. For a review of PCR technology, see White (1997) B. A. Ed. in Methods in Molecular Biology 67: Humana Press, Totowa; Erlich, (1992) PCR Technology; Principles and Applications for DNA Amplification. W. H. Freeman and Co., New York; and the publication entitled "PCR Methods and Applications" (1991, Cold Spring Harbor Laboratory Press), which disclosures are hereby incorporated by reference in their entireties.

When the initial polynucleotide sample contain mostly RNA, double stranded cDNAs are first synthesized using any technique known to those skilled in the art including those described previously in the section labeled "Preparation of complex polynucleotide sample". Then, cDNAs of interest derived from a single gene or a limited set of genes are selectively amplified from said double stranded cDNA sample with primers specific to the single gene or to the limited set of genes of interest, using preferentially the PCR technique ("Current Protocol in Molecular Biology", Volume 2, Chapter 15). Indeed, at least one couple of primers is specifically designed for each gene of interest as follows. Preferably, the first oligonucleotide primer is designed to anneal as close as possible to the 5' end of the cDNAs of interest and the second oligonucleotide primer to anneal as close as possible to the 3' end of the cDNAs of interest. Optionally, several couple of primers may be designed to hybridize to different alternative most 3' exons or 5' exons for the same gene based either on experimental knowledge already accumulated concerning the existence of alternative 5' and/or 3' exons or on the prediction for alternative splicing using database searches and any software known by those skilled in the art. Thus, as will be readily apparent to those skilled in the art, a targeted mixture of double-stranded cDNA molecules corresponding to each targeted gene is obtained, wherein different splicing isoforms of said targeted genes are represented when the alternative splicing events occur in the region located between the two PCR primers. When a targeted cDNA sample derived from several genes is desired, PCRs may be carried out in parallel either in the same tube or, preferably when the set of genes is large, in different aliquots of the initial cDNA sample that are then pooled together to obtain the final targeted cDNA sample.

Similarly, when the initial polynucleotide sample contains mostly genomic DNA, the targeted DNA sample is preferably obtained by PCR, more preferably using the long-range PCR technique, with primers specific to the specific gene or limited set of genes of interest. Preferably, the first oligonucleotide primer anneals to the most 5' end of the gene(s) of interest and the second oligonucleotide primer anneals to the most 3' end of the portion of the gene(s) of interest. Hence, the resulting product is a double-stranded polynucleotide sample comprising the different polynucleotide species arising from a single gene or a limited set of genes.

Alternatively to preparation of a targeted polynucleotide sample, the nucleic acid differences existing for a given polynucleotide species or a limited set of polynucleotide species, and polynucleotides thereof, may be selected and isolated at a later step of the method according to the invention using any method known to those skilled in the art. For example, polynucleotide species of interest may be isolated from a complex polynucleotide sample enriched in polynucleotides harboring nucleic acid differences using any specific labeled oligonucleotide probe allowing retrieval of the hybridized polynucleotides of interest.

Reduction of the Polynucleotide Sample

Optionally, a reduction step may be performed to prepare the initial polynucleotide sample that is either a complex or targeted polynucleotide sample. Alternatively, a reduction step may be performed at any convenient step of the isolation process, and even after said selection step. Reduction is a process by which the polynucleotides of interest are cut into smaller fragments in order to facilitate the ultimate step of actual identification of nucleic acid differences, preferably using sequencing techniques. The sequencing step is more efficient and economic if the polynucleotide can be sequenced by a single 5' and/or 3' pass. Therefore, the size of the fragment should preferably not exceed 1000 bp. Preferably, the length of the fragment is between 400 and 1000 bp, more preferably about 700 bp.

Such reduction may be achieved by fragmentation that allows to reduce the size of the polynucleotide to about 1000 bp or less. The fragmentation may be achieved by any method known in the art, for example, enzymatically, chemically, mechanically, etc.

In a preferred embodiment, the polynucleotides are broken up by a mild digestion with bovine pancreatic DNase I. This enzyme produces double strand scission of DNA in the presence of $Mn^{2+}$ The cleavage is random and can be controlled by varying the enzyme concentration, temperature and/or incubation time. In another embodiment, fragmentation can be achieved by sonication or by digestion with other endonucleases, for example restriction endonucleases.

Optionally, the fragmentation products can be further processed in order to select fragments with an appropriate size, preferably a size of 1000 bp or less. For example, resulting fragmentation products may be separated by gel electrophoresis and the bands corresponding to 400–1000 bp may be excised from the gel and recovered by one of the numerous existing methods. Alternatively, polynucleotide fragments may be separated by column chromatography or other methods known in the art.

A polynucleotide sample subjected to a reduction step is referred to herein as being "reduced".

The Annealing Step

The aim of this step is to allow annealing of single stranded molecules from a M0 polynucleotide sample into duplexes containing strands that are complementary at least over a region, thus forming duplexes that are at least partly double stranded. However, if the polynucleotide sample M0 contains mostly double stranded molecules, an additional step of denaturation prior to annealing is necessary to obtain single stranded molecules.

The term "denaturation", as used herein, refers to the process by which a double-stranded nucleic acid molecule is converted into its constituent single strands, one having a (+) polarity and the other one a (−) polarity, by breaking the bonding between complementary bases on both strands.

The terms "annealing", "renaturation" and "hybridization", as used interchangeably herein, refer to the process of joining two nucleic acid strands, one being a (−) strand and the other one a (+) strand, to form a double-stranded molecule, or duplex, wherein said joining is mediated by hydrogen-bonding between complementary bases on both strands. These nucleic acid strands can either be two DNA strands or one DNA strand and one RNA strand or two RNA strands.

Denaturation of Double-stranded Molecules

In the denaturation process, The M0 polynucleotide sample is exposed to denaturing conditions so that individual nucleic acid strands within the sample are separated from one another and hence, most if not all the polynucleotides present in M0 become single-stranded molecules. Denaturation may be achieved, for example, by the use of high temperature, preferably temperature above 95 degree Celsius, low ionic strength, acidic or alkaline pH, and/or certain solvents such as formamide or urea. Methods for denaturing nucleic acids are well-known in the art (see, for example, experimental details in material and methods of Cotton et al. Proc. Natl. Acad. Sci. USA 85:4397, 1988; Shenk et al. Proc. Natl. Acad. Sci. USA 72:989, 1975; Steger Nuc. Acids Res. 22:2760, 1994; each of which is incorporated herein by reference).

Annealing of Single Stranded Molecules

The polynucleotide sample containing only or mostly single stranded molecules is exposed to annealing conditions so that individual strands anneal to one another. Annealing conditions are those values of, for example, temperature, ionic strength, pH and solvent which will allow annealing to occur. Conditions promoting annealing such as high ionic strength and/or lower temperatures, and the variation of these conditions to adjust the stringency of hybridization are well-known in the art (Sambrook et al, 1989, supra; Ausubel et al. Current Protocols in Molecular Biology, supra) including the PERT technique where hybridization is realized in a phenolic emulsion maintained in thermocyclers (Kohne et al., (1977) Biochemistry, 16 N°24, 5329–5341) or by agitation (Miller and Riblet, Nucl. Acid. Res. (1995) 23: 2339), which disclosures are hereby incorporated by reference in their entireties. The time of annealing can be varied depending on the complexity of the sequences in the reaction and the extent of hybridization desired. Annealing conditions can also be adjusted to favor the level of complementarity desired.

Preferably, annealing is performed within a liquid phase or on an appropriate support using any appropriate means (such as Eppendorf tubes for example). More preferably, the hybridization is carried out in small volumes, preferably between 10 and 1000 microliters, more preferably between 10 and 500 microliters. Quantities of nucleic acid materials may be determined by a man skilled in the art. Generally quantities between 0,1 to 100 micrograms are used.

A polynucleotide sample subjected to an annealing step is referred to herein as being "annealed".

The denaturation and annealing steps generate several structural types of molecules, some of which are schematically drawn in FIG. 1.

Type alpha molecules: these molecules are perfect or almost perfect double-stranded duplexes or homoduplexes. For example, this type of molecule is formed when a full length single-stranded cDNA corresponding to one splicing isoform of a given gene anneals with a complementary full length cDNA strand corresponding to the same isoform.

Type beta molecules: these molecules are imperfect duplexes harboring a single-stranded tail at one or both ends. For example, phenomenon such as mRNA degradation, premature stop of the reverse transcription, internal priming can lead to the production of truncated cDNA strands. When a truncated cDNA strand anneals with a non truncated complementary strand, the newly formed duplex will have a single-stranded tail at one or both ends. Alternatively, such duplexes may form between two strands belonging to different splicing isoforms of the same gene, one isoform being characterized by the addition or deletion of an exonic region at one end compared to the other.

Type gamma molecules: these molecules are heteroduplexes having one or more internal single-stranded regions characterized by the presence of a single-stranded tail at one or both ends. For example, such molecules are obtained when a truncated cDNA strand corresponding to a splicing isoform of a gene anneals with a full length complementary strand of another isoform of the same gene, wherein the isoforms share common exons at both their 5' and 3' end. When isoforms only differ by the insertion or deletion of a region, an internal single stranded loop is formed. When isoforms only differ by the replacement of a region by another one, an internal single stranded bubble is formed.

Type delta molecules: these molecules are heteroduplexes having one or more internal single-stranded regions characterized by the absence at their extremities of single-stranded tails. For example, this type of molecules are formed when a full length cDNA strand corresponding to one splicing isoform of a gene anneals with a full length complementary cDNA strand corresponding to an another isoform of the same gene, wherein the isoforms share common exons at both their 5' and 3' end. Alternatively, these structures exist when a strand from a genomic DNA anneal with the complementary strand of genomic DNA corresponding to the same gene but containing a mutation characterized by an insertion or deletion of a region.

Type sigma molecules: the molecules are entirely single-stranded molecules. This population of single-stranded molecules corresponds to the population of individual strands produced by the denaturation step that did not anneal to another strand.

The heteroduplexes with an internal single-stranded regions(s) or ISSRHs, represented in FIG. 1 by gamma and delta molecules, are the molecules of interest encompassed by the following invention because they comprise a nucleic acid difference corresponding for example to an alternative splicing event, to a genomic insertion or deletion, or to a sequence repeat extension. Indeed, two single stranded polynucleotides complementary except for a nucleic acid difference will form a double-stranded molecule with one or more internal single-stranded region(s) corresponding to said nucleic acid differences between the two polynucleotides.

The Cleaning and Blunting Steps

In order to increase the efficiency of the single stranded trap to select ISSRHs, <<parasitical>> single-stranded regions present on some molecules of the annealed sample, that is to say all the single-stranded DNA regions that do not correspond to an internal region such as completely single-stranded molecules (sigma molecules in FIG. 1) or single-stranded ends of duplexes (beta and gamma molecules in FIG. 1) may be removed using a cleaning procedure eventually completed by a blunting procedure. More particularly, the single-stranded ends of the type beta and gamma molecules are eliminated as well the complete single-stranded type sigma molecules. Thus, type gamma molecules are transformed into type delta molecules and type beta molecules into type alpha molecules.

The terms "clean", "cleaning" or "cleaned", as used interchangeably herein, refer to the partial or total elimination of single-stranded regions other than internal single stranded regions from the polynucleotides in the sample of interest.

The cleaning step is used to substantially reduce the presence of single-stranded fragments different from internal single-stranded regions that would preclude the efficiency and the specificity of the single-stranded trap for ISSRHs. It is an optional step that is however mandatory when the initial sample is subjected to a random reduction step.

A variety of techniques are available in the art for removal of single-stranded ends from a nucleic acid duplex and for elimination of single-stranded molecules. For example, single-stranded ends and free single-stranded molecules can be digested using a single-strand-specific exonuclease such as exonuclease VII (Kroeker et al. Biochemistry 15:4463, 1976, incorporated herein by reference). Exonuclease VII, which digests single-stranded DNA from either 5' or 3' end but cannot act on single-stranded DNA without free ends, will digest the single-stranded tails of types beta and gamma molecules and remove type sigma molecules but will not act on the internal single-stranded regions of ISSRHs. It is important to note that exonuclease VII is not suitable for blunt-ending double-stranded DNA, as its mode of action may result in single nucleotide overhangs remaining after treatment. Other enzymes having similar appropriate enzymatic properties may be used.

In one preferred embodiment, the cleaning step is carried out with an exonuclease able to digest single stranded nucleic acid molecules, preferably exonuclease VII.

The terms "blunt", "blunting" or "blunted", as used interchangeably herein, refer to the modification of the ends of double stranded polynucleotides in order to obtain polynucleotides in which the ends of both strands are even with each other rather than one strand being longer than the other.

This blunting step is an optional step that may be carried out without any previous cleaning step but it is preferably performed in addition to the cleaning step. It serves two purposes: i) contributing to the elimination of single-stranded ends that may preclude the efficiency and the specificity of the single-stranded trap, synergistically to the cleaning step and ii) prepare duplex ends for an eventual adapter ligation. However, the blunting step is mandatory when a random reduction step is performed leading to fragments with non blunt ends and that an adapter ligation is desired.

Another advantage of this blunting steps is to convert, whenever it is necessary or desired, polynucleotides in a form that is suitable for subsequent amplification of the polynucleotides recovered after the selection step using the single-stranded trap of the invention. Such an amplification will allow, if necessary, to perform a new enrichment cycle for isolating related polynucleotides harboring nucleic acid differences. The conversion of polynucleotides present in the annealed sample in a form that can be amplified by PCR may be carried out by ligation of an adapter to the polynucleotide ends. However, as will be readily apparent to one of ordinary skill in the art, a blunting step will most often be an essential prior condition to the ligation step.

Techniques for blunt-ending double-stranded DNA are well known in the art (see Hyone-Myong Eun, chapter 6, pp 367, 368 and 382, 383 in *Enzymology Primer for Recombinant DNA Technology*, Academic Press, 1996; Gubler, Methods Enzymol. 152:330, 1987; Sambrook et al. supra pg. 5.45; each of which is incorporated herein by reference). They involve the use of DNA polymerases such as T4 DNA polymerase or the Klenow fragment (Pol Ik) of *E. coli* DNA polymerase I. For example, T4 DNA polymerase which exhibits both a 3'→5' exonuclease activity and a 5'→3' DNA polymerase activity, will complete digestion of protruding 3' ends of double-stranded DNA molecules and will fill in the gap due to recessive 3' end to produce DNA molecules with blunt ends.

In one preferred embodiment, the blunting step is carried out with a polymerase, preferably the T4 DNA polymerase or the Klenow fragment of *E. coli* DNA polymerase I. In a more preferred embodiment, the blunting step is carried out using the T4 DNA polymerase.

Single-stranded Trap

An important step of the methods of the present invention is the isolation of the population of heteroduplex molecules harboring internal single-stranded region(s) or ISSRHs, from the rest of the sample. By separating this subset of ISSRHs from the rest of the polynucleotides nucleic acid differences may then be identified very easily.

In the present invention, the population of ISSRHs is selected and isolated with a single-stranded trap, i.e, a means to select the molecules comprising a single-stranded region in a sample. The single-stranded trap of the invention is based on a "Recognition Element" (RE) having a preferential affinity for single-stranded polynucleotides compared with double stranded polynucleotides, preferably under conditions used to bind to single stranded polynucleotides. By referential affinity, it is understood that the RE has a higher affinity for single-stranded olynucleotides than for double-stranded polynucleotides. Preferably, said affinity for single stranded polynucleotides is at least $10^1$, $10^2$, $10^3$, $10^4$, $10^5$, $10^6$, $10^7$, $10^8$ or higher than said affinity or double stranded polynucleotides.

In a preferred embodiment, the RE has a high affinity for single-stranded DNA but almost no affinity, more preferably no affinity, for double stranded DNA or single stranded RNA under conditions used to select single stranded DNA. More preferred are REs that have a referential affinity for DNA as compared to RNA, more preferably almost no affinity for RNA, still more preferably no affinity for RNA under conditions used to select DNA In another preferred embodiment, the recognition element has a high affinity for single-stranded RNA but almost no affinity, more preferably no affinity, for double stranded RNA. Further preferred are REs that have a preferential affinity for RNA as compared to DNA, more preferably almost no affinity for DNA, still more preferably no affinity for DNA under conditions used to select RNA.

Use of Proteins as Recognition Elements

A set of preferred RE of the invention are peptides and proteins having a preferential affinity for single-stranded polynucleotides compared with double stranded polynucleotides. In a preferred embodiment, said RE has a high affinity for single-stranded DNA but almost no affinity, more preferably no affinity, for double stranded DNA or single stranded RNA under conditions used to select single stranded DNA. More preferred are RE with an affinity for single stranded DNA in the range of $10^8$–$10^{11} M^{-1}$ whereas their affinity for double stranded DNA does not exceed $10^4$–$10^5 M^{-1}$. Further preferred are REs that have a preferential affinity for DNA as compared to RNA, more preferably almost no affinity for RNA, still more preferably no affinity for RNA under conditions used to select DNA RE of the present invention may be described or specified in terms of their binding affinity for single-stranded polynucleotides. Preferred binding affinities include those with a dissociation constant or Kd less than $5 \times 10^{-6}$M, $10^{-6}$M, $5 \times 10^{-7}$M, $10^{-7}$M, $5 \times 10^{-8}$M, $10^{-8}$M, $5 \times 10^{-9}$M, $10^{-9}$M, $5 \times 10^{-10}$M, $10^{-10}$M, $5 \times 10^{-11}$M, $10^{-11}$M, $5 \times 10^{-12}$M, $10^{-12}$M, $5 \times 10^{-13}$M, $10^{-13}$M, $5 \times 10^{-14}$M, $10^{-14}$M, $5 \times 10^{-15}$M, and $10^{-15}$M.

Preferred RE of the inventions are proteins known as single-stranded binding proteins (SSB). SSBs are defined herein as binding proteins with a strong preference for DNA over RNA, and for single-stranded DNA over duplex DNA. SSBs bind tightly and cooperatively, and do not catalyze other enzymatic activities such as the DNA-dependent ATPase activities found in helicases and topoisomerases. SSBs are found both in prokaryotes and eukaryotes. The best-studied prokaryotic SSBs are the product of gene 32 of phage T4 (gp32) and the *Escherichia coli* SSB. *E. coli* SSB and gp32 may be purchased from Promega (M3011) and Ambion (2422) respectively. The best-studied eukaryotic SSBs are the adenovirus DBP and calf thymus UP1. (for more information about SSB proteins, see Kornberg and Baker, Chapter 10, in *DNA Replication, second edition* W. H.Freeman and Company, New York; and Chase (1986) Ann. Rev. Biochem. 55:103–36, which disclosures are hereby incorporated by reference in their entireties). Encompassed by the invention as RE are homologues or variants of SSBs that retain a preferential affinity for single stranded DNA compared to double stranded DNA.

In other embodiments of the invention, others proteins binding to single-stranded DNA to varying degrees of specificity, such as RNA polymerase, recombinases such as RecA and UVsX, glyceraldehyde-3-phosphate dehydrogenase, and lactate dehydrogenase, as well as their homologues or variants, may be used as RE (Grosse et al. Eur J Biochem (1986) 160(3):459–67; Chase et al (1986) supra; Ando and Morrical (1998) 283:785–96).

In still another embodiment, the RE is an antibody able to bind selectively to single-stranded polynucleotides (DNA, RNA, or both). Generally, antibodies specific for single-stranded polynucleotides are those with a specificity directed against the purine and pyrimidine nucleotides. Indeed, accessible purine and pyrimidine nucleotides are present in single-stranded polynucleotides and not in double-stranded polynucleotides. Examples of antibodies that could be used as RE are: autoantibodies binding to single stranded DNA as those found in several rheumatic diseases, in certain types of cancer and other diseases such as Systemic Lupus erythematosus (Swanson et al, Biochemistry 1996 36:1624–33; Stevens and Glick, Biochemistry 1999 38:560–8, which disclosures are hereby incorporated by reference in their entireties). Such antibodies specific for single stranded DNA may be purchased form Scimedex (ref SSD96). Alternatively, libraries of antibodies could be screened in order to find antibodies presenting a preferential affinity for single stranded polynucleotides compared to double stranded polynucleotides using any method known to those skilled in the art. Alternatively, monoclonal or polyclonal antibodies with a preferential affinity to single stranded polynucleotides may be produced using any techniques known to those skilled in the art.

In still another embodiment, the RE is a peptide having a preferential affinity for single stranded polynucleotides (DNA, RNA or both) compared to double-stranded polynucleotides. Such peptides may be found by screening peptide libraries containing tens of millions of peptides. Peptide libraries may be constructed on bacterial phages or obtained from direct chemical synthesis. For example, in the phage peptide library method, a random gene of a given length is synthesized and inserted into the bacterial phage gene. Once the peptide sequences of interest are identified, they can be chemically synthesized. This concept has been described in detail by Baumbach and Hammond, BioPharm., May 24, 1992, which disclosure is hereby incorporated by reference in its entirety.

It should be noted that a RE able to recognize a nucleic acid difference of a desired length or range of length may be used. Such RE may be developed using methods known to those skilled in the art including screening of antibodies or peptide libraries and in vitro protein evolution techniques such as DNA shuffling and DNA family shuffling [for examples of these shuffling strategies, see Yano, T et al, (1998) Proc. Natl. Acad. Sci. USA 95, 5511–5515; Zhang, J. H., et al (1997) Proc. Natl. Acad. Sci. USA 94, 4504–4509; Chang, C.-C., et al (1999) Nat. Biotechnol. 17, 793–797; Kikuchi, M., et al (2000) Gene 243, 133–137].

Selection Step

The selection step is carried out as follows. The recognition element is mixed with the polynucleotide sample in solution so that the binding of the RE to the single stranded regions of the polynucleotides within the sample occurs in solution. After this binding step, the RE-polynucleotide complexes are separated from the rest of the free polynucleotide in the sample. As will be readily apparent to one of ordinary skill in the art, a lot of possibilities exist for separating proteins or peptides bound to polynucleotides from free polynucleotides. These possibilities may be classified in two major categories.

In the first category, separation is achieved using general properties that distinguish proteins or peptides from polynucleotides. For example, separation of protein bound to polynucleotides from free polynucleotides may be carried out using nitrocellulose filters because nitrocellulose has the ability to bind proteins but not double-stranded DNA (see, for example, Current Protocols in Molecular Biology, Volume 2, Chapter 12, supra), which disclosure is hereby incorporated by reference in its entirety. Another possibility for isolating polynucleotides interacting with a protein from free polynucleotides is to perform extraction with a solvent such as 1:1 phenol-chloroform (see Invitrogen, San Diego, Calif. 1995 catalog page 63).

In the second category, separation is achieved by affinity techniques in which the target molecule, i.e. RE, is captured by an immobilized ligand. In a first subcategory, the ligand has affinity for the target per se, i.e. the target protein or peptide in an unmodified form. For example, many conventional affinity protein purification processes use monoclonal antibodies as immobilized affinity ligands. Thus, for example, if the RE is a SSB protein, the complexes formed between the SSB and the ISSRHs could be separated from the rest of the sample by using, as an immobilized ligand, an antibody binding specifically to the SSB protein.

In a second subcategory, the RE is modified in order to contain an affinity site for an immobilized ligand. For example, the RE may be biotinylated. Then, the biotinylated RE and the polynucleotide sample are mixed together and the complexes formed during this binding step between the biotinylated RE and polynucleotide molecules harboring single-stranded regions are separated from the rest of the polynucleotide sample using one of the numerous biotin/streptavidin purification systems. Another strategy for modifying a RE is to produce a recombinant RE protein containing a fusion tag added to the RE. In this strategy, a polynucleotide encoding a peptide or protein tag (also called, among other names, affinity tails, cleavable linkers, and marker sequences) is attached to the gene of interest (for example the gene of the $E.$ $coli$ SSB protein) at its 5' or 3' end. The resulting gene fusions are expressed in a host cell and the encoded recombinant fusion protein isolated from contaminating host proteins based on properties of the engineered tag using methods known in the art. Using this strategy (which is sometimes referred to as the affinity-tag protein purification system), a purified tagged RE protein is obtained that can be used to separate polynucleotide molecules harboring single-stranded regions from the rest of the polynucleotide sample. For example, complexes between a tagged SSB protein and polynucleotide molecules harboring single-stranded region are allowed to form in solution. These complexes are then removed from solution by running the sample through an affinity matrix on which an affinity ligand that bind specifically to the tag has been immobilized.

In the methods described above, the RE is first allowed to form a complex with its single-stranded polynucleotide target in solution during a so-called binding step. The RE-polynucleotide complex is then purified from free polynucleotides. As a further embodiment of the present invention, these two steps may be combined and performed simultaneously. For example, the RE may be immobilized on a solid matrix and the sample applied to this affinity matrix in order to separate the polynucleotides with single-stranded regions from polynucleotides without an single-stranded region.

In a preferred embodiment of the invention, the single-stranded trap is designed as follow. The RE is a "single-stranded binding protein", preferably the $Escherichia$ $coli$ SSB. Binding of SSB with ISSRHs occur in a buffer with a relatively high ionic strength, preferably between 0,2M and 0,8M NaCl, more preferably around 0, 3 M NaCl. Under these ionic conditions, the binding of $E$ $coli$ SSB is highly specific for single-stranded DNA.

In a more preferred embodiment, the $E.$ $coli$ SSB has been genetically engineered to harbor a purification tag, preferably a His-tag, either at its NH2 or COOH terminus. The His-tag SSB is mixed with the polynucleotide sample of interest so that complexes between the tagged SSB and polynucleotide harboring single-stranded region form in solution. These complexes are then removed from solution by running the sample through an Immobilized Metal Affinity Chromatography (IMAC) matrices designed for purification of His-tag fusion proteins. Such IMAC matrices, well known in the art for affinity purification of tagged proteins, may be purchased from a variety of sources (such as, for example, Novagen). His-tag SSB/DNA complexes are then eluted by using a competitive counter-ligand, preferably imidazole, or a buffer with a very high ionic strength.

Optionally, the isolated ISSRH-RE complexes are treated in order to release ISSRHs of interest from RE using any techniques known to those skilled in the art to separate polynucleotides from polypeptides. For example, a phenol chloroform extraction eventually followed by a chloroform extraction and an alcohol precipitation step may be carried out. Alternatively, the ISSRH-RE complexes may be treated with a protease or cocktail of proteases to degrade the proteic part of the complex and subsequently retrieve the nucleic acid part, namely the ISSRHs.

Optionally, the selection of ISSRHs using the single stranded trap of the invention may be repeated several times on the same sample, preferably using fresh RE, in order to maximize the recovery of ISSRHs from the sample. Preferably, said selection is carried out 1 to 5 times. The optimum number of repetitions will depend primarily on the relative amounts of the ISSRHs to be trapped and the quantity of RE available for trapping in each round.

One of ordinary skill in the art will appreciate that the above described techniques to select ISSRHs from a polynucleotide sample represents a description of some of the embodiments of the present invention. Various changes and modification will be obvious to the man skill in the art and can be made without departing from the spirit or scope of the present invention.

Use of Materials as Recognition Elements

Recognition elements also encompassed by the invention are those materials exhibiting preferential affinity for single stranded polynucleotides compared to double stranded polynucleotides. Such material may be any support or substance to which single stranded polynucleotides preferentially associate compared to double stranded polynucleotides in a reversible manner, irrespectively of the nature of the association between said polynucleotides and said material. Such association may be absorption, adsorption, or any other reversible type of association.

Preferred materials to be used as RE are those supports used to fractionate polynucleotide samples and that are able to retain specifically single stranded polynucleotides including but not limited to methylated albumin columns such as MAB (methylated albumin on bentonite column) or MAK (methylated albumin on Kieselgur column), or a benzoylated-naphthoylated DEAE cellulose (BNDC) column.

In a preferred embodiment of the invention, such materials are used to prepare columns using techniques known to those skilled in the art. Preferably, such material are packed into disposable syringes. After a washing step, the polynucleotide sample is run through the column which retains preferentially single stranded polynucleotides. Conditions of binding depend on the type of support used and may be easily figured out by anyone skilled in the art. If a MAK column is used, a preferred washing and binding buffer is a buffer adjusted to pH 6.7 with an ionic strength comprised between 0.6 M NaCl and 1.6 M Nacl. If a BNDC column is used, a preferred washing and binding buffer is a 1M NaCl buffer. After optional but preferred washing steps, retained single stranded polynucleotides are then eluted from the column using any methods known to those skilled in the art to disrupt the type of association formed between said retained single stranded polynucleotides and said support. For example, a buffer with a higher ionic strength is used. Sometimes a stepwize salt gradient may be used. Eventually, a buffer with different pH conditions may be used. If a MAK column is used, elution is preferably performed with i) a stepwize salt gradient ranging from the ionic strength of the binding buffer to 1.6M NaCl, and eventually ii) a 1M NaCl, buffer adjusted to pH 7, 10.7 and then 11.6. If a BNDC column is used, elution is preferentially performed with a 1M NaCl buffer containing 50% formamide. More details on experimental conditions may found for BNDC and MAK in Davies and Miller, J Lab Clin Med (1981) 98:549–57; for BNDC in Nelson et al., Nature Genetics (1993) 4:11–17; for MAK in Braun, Z. Naturforsh. (1975) 30:248–252; for MAB in Shirobokov et al., Biokhimiaa (1975) 40:531–537), which disclosures are hereby incorporated by reference in their entireties.

Optionally, the selection of ISSRHs using the single stranded trap of the invention may be repeated several times on the same sample by running the sample onto said column in order to maximize the recovery of ISSRHs from the sample. Preferably, said selection is carried out 1 to 5 times. The optimum number of repetitions will depend primarily on the relative amounts of the ISSRHs to be trapped and the quantity of RE available for trapping in each round.

One of ordinary skill in the art will appreciate that the above described techniques to select ISSRHs from a polynucleotide sample represents a description of some of the embodiments of the present invention. Various changes and modification will be obvious to the man skill in the art and can be made without departing from the spirit or scope of the present invention.

The polynucleotide population obtained after the selecting step is enriched in ISSRHs. Such enriched population may be cloned to obtain libraries enriched with polynucleotides containing nucleic acid differences. These differences may then be precisely identified by sequencing the enriched library. Alternatively, if the enrichment is not sufficient, another cycle of enrichment may be performed before the cloning step.

Adapter Ligation and Cleavage

Optionally, an adapter is used in the methods according to the present invention to allow subsequent cloning or subsequent amplification of the polynucleotides of interest. Therefore, the goal of the adapter ligation step is to convert the selected polynucleotides to a form which is suitable for further cloning or amplification. As will be readily apparent to one of ordinary skill in the art, such ligation of adapter sequences to polynucleotides will not only allow the amplification of the polynucleotides that were recovered from the selection step by the single-stranded trap, therefore making the final cloning step easier, but will also, if necessary, allow to relaunch a new enrichment cycle.

The adapter must be long enough to contain at least one binding site for an amplification primer and to act as an efficient hybridization site for subsequent amplification. Preferably, the adapter is 10 to 40 nucleotides in length. More preferably, the adapter is 20 to 30 nucleotides in length. Preferably, the primer is also designed in order to be easily removed when necessary or desirable. For example, the adapter may harbor a restriction site anywhere within its sequence, i.e. near the end that will be ligated to the polynucleotides of interest (ligation site), near the free end (distal site), or internally, but preferably near the ligation site. The adapter containing a restriction enzyme site may then be removed at least partially or totally, depending on the position of the restriction site within the adapter, by a simple digestion of the polynucleotide sample with the suitable restriction enzyme. Preferably, rare restriction sites are chosen, including but not limited to Not I, Eco RI, Hind III, so that when the adapter is removed, very few undesirable internal cuts within the polynucleotides of interest occur. Undesirable cuts in this context are the ones that could prevent correct nucleic acid difference identification, that is to say mainly the ones that would occur either within the region harboring said nucleic acid differences or within its immediate surroundings. More preferably, the adapter sequence include multiple restriction enzyme sites, even more preferably multiple rare restriction sites, for ease and flexibility in subsequent cloning. Such oligonucleotide adapters may either be completely artificially synthesized using any material and method known to those skilled in the art, including chemical synthesis, or purchased from commercial supplier.

A preferred adapter is formed by the annealing of two complementary single stranded oligonucleotides of different sizes, the longer one being one to three nucleotides longer. Only the short one is phosphorylated at its 5' end. The two oligonucleotides are designed in such a way that the ligation site of the adapter is blunt whereas the distal site displays a 5' single-stranded tail of one to three nucleotides. The role of this 5' protruding region at the distal site is to avoid any adapter polymerization process during the ligation step.

Adapters may be ligated to the ends of polynucleotides using techniques well-known in the art. Adapters may be attached chemically or enzymatically. Preferably, polynucleotides are ligated to adapters using T4 DNA ligase. The adapter is preferably attached to blunted ends of polynucleotides.

Optionally, ligated adapters are cleaved from polynucleotides in the methods according to the present invention. Preferably, adapters are cleaved with an appropriate restriction enzyme. The cleavage of the adapters is an optional step for the cloning. Therefore, as alternative embodiments, the adapters are either fully or partially removed before the cloning step or are cloned intact.

Amplification

This optional step of amplifying the polynucleotides isolated using any method of the invention serves two purposes: i) increasing the amount of isolated polynucleotides obtained in order to increase the efficiency of subsequent steps such as cloning, sequence analysis or even another round of enrichment, and ii) increasing the efficiency of cloning of isolated nucleic acid differences by avoiding eventual reparation of internal single stranded regions by recombinant bacteria.

Amplification may be performed using any techniques known to those skilled in the art including those disclosed herein, especially in the section entitled "Preparation of targeted polynucleotide sample". PCR is the preferred technique of amplification.

In order to perform PCR, polynucleotide ends must be known. Therefore, an adapter ligation step is most often necessary prior to amplification. Alternatively, adapter ligation is not mandatory when the polynucleotide ends are known and homogeneous, as in the case of an initial polynucleotide sample targeted using PCR and not submitted to a reduction step (see examples 4 and 7).

In the case an adapter was ligated, primers may be specifically designed to amplify such isolated polynucleotides. Preferably, such primers are designed to be able to hybridize specifically to the ligated adapter.

In the case the initial polynucleotide sample was submitted to a targeted step using PCR without any reduction step, primers to amplify isolated polynucleotides may be the same that those used to prepare the targeted polynucleotide sample or primers internal to those used to prepare the targeted polynucleotide sample.

Cloning

The isolated polynucleotides comprising nucleic acid differences may then be cloned in appropriate vectors to provide libraries enriched in related polynucleotides harboring nucleic acid differences using any techniques know to those skilled in the art such as those described in Sambrook et al., supra, Volume 1, Chapters 1, 2 and 3, and Volume 2, Chapter 8, incorporated herein by reference in its entirety. A wide variety of cloning vectors are available that replicate in a host cell, and techniques for introducing foreign polynucleotides into a cloning vector are well established, even when the nucleotide sequence is unknown (Klickstein et al. Current Protocols in Molecular Biology, Ausubel et al. eds, supra, pp 5.5.1–5.5.14, incorporated herein by reference in their entireties.

Vectors used for cloning are well known to those skilled in the art and may be plasmids, cosmids, YAC, HAC, phages, etc. Vectors are available that are specifically designed to allow easy sequence determination (e.g., Promega, Madison, Wis., 1994/95 catalog #P2211, #P2551), easy production of RNA probes (e.g., Promega, Madison, Wis. 1994/95 catalog #P2129, #P2221, #P1091, #P1101, #P1241, #P2211, #P2551, #Q6301, #Q6121, #Q6111; see also RNA probe production kits from Promega, Madison, Wis. 1994/95 catalog #P1280, #P1300, #P1290, #P2020, #P1270, #P1071, #P1250, #P2580, #P2590), easy expression of polypeptides encoded by cloned products (e.g., Promega, Madison, Wis. 1994/95 catalog #P2211, #P2551, #Q6111; see also in vitro translation kits from Promega, Madison, Wis. 1994/95 catalog #L4540, #L4970, #L4152, #L4330, #L4140, #L4410, #L1030, #L1020), etc. For example, the cloning is proceeded with TOPO TA Cloning Kit (Invitrogen San Diego, Calif. Catalog #K4500-01). If necessary, polynucleotide probes can be made using any of these vectors, for example, by removing out the cloned insert and labeling it using nick translation or random priming methods (see, for example, Sambrook et al., supra, Chapter 10, incorporated herein by reference in its entirety).

Recombinant vectors are introduced into an appropriate host cell, and replicated therein, according to known procedures (see, for example, Sambrook et al. supra, pp.1.74–1.75, incorporated herein by reference in its entirety). Specific vectors are available that are designed to replicate in virtually any host cell, such as a bacterial cell, a yeast cell, a mammalian cell, a fruit fly cell, etc. (see, for example, Invitrogen, San Diego, Calif. 1995 catalog #V780-20, #V044-50, #V004-50; see also Yates et al. Nature 313:812, 1985, incorporated herein by reference in its entirety). To avoid reparation of internal single stranded regions of selected polynucleotides containing ISSRHs by recombinant bacteria, a PCR amplification step may be performed prior to cloning. Alternatively, bacteria strains defective in DNA repair systems may be used.

Cloning inherently separates individual isolated fragments from one another. Optionally, a separation step prior to cloning may be carried out using any techniques known to those skilled in the art. For example, polynucleotides selected with the SST may be separated by gel electrophoresis, and fragments of a particular size, or range of sizes, isolated from fragments of other sizes. Individual size-fractionated populations may then be cloned into vectors.

Libraries Enriched in Nucleic Acid Differences

Libraries enriched in related polynucleotides comprising nucleic acid differences are encompassed by the present invention. The term "library enriched in polynucleotides comprising nucleic acid differences" refers to a library comprising the polynucleotides selected by a single-stranded trap according to the present invention. A library enriched in nucleic acid differences may be described with a percent enrichment, whereby the library contains anywhere from 1% to 100% nucleic acid differences, whereby any integer between 1 and 100, inclusive, are included as specific embodiments of the present invention. The above embodiments may be expressed as "at least" "X" percent nucleic acid differences whereby "X" equals any integer between 1 and 100 inclusive. Alternatively, the level of nucleic acid differences enrichment may be expressed as a fold increase or "at least" a fold increase, whereby the fold increase of nucleic acid differences to non-nucleic acid differences or heteroduplex to non-heteroduplex polynucleotide is any integer between 2 and 10,000 inclusive.

The invention encompasses any library enriched in polynucleotides comprising nucleic acid differences characterizing a given situation (e.g. physiological, environmental, experimental, or natural). The invention encompasses also any library enriched in polynucleotides comprising nucleic acid differences characterizing different situations (e.g. different tissues, pathologic vs healthy). Depending on the initial polynucleotide sample M0 and depending on whether a reduction step was carried out or not, four types of libraries may be obtained:

when the initial polynucleotide sample was a complex polynucleotide sample that was not subjected to a reduction step, isolated polynucleotides form a library of polynucleotides comprising nucleic acid differences. For example, using this technique, libraries of cDNAs corresponding to isoforms of genes subjected to alternative splicing events may be obtained.

when the initial polynucleotide sample was a complex polynucleotide sample that was subjected to a reduction step, isolated polynucleotides form a library of polynucleotide fragments comprising nucleic acid differences. For example, using this technique, libraries enriched in alternative splicing events, i.e. in fragments containing said differences and surrounding sequences, rather than full-length splicing isoforms, may be obtained.

when the initial polynucleotide sample was a targeted polynucleotide sample that was not subjected to a reduction step, isolated polynucleotides form a library enriched in polynucleotides comprising nucleic acid differences arising from a single gene or a limited set of genes.

when the initial polynucleotide sample was a targeted polynucleotide sample that was subjected to a reduction step, isolated polynucleotides form a library of polynucleotide fragments comprising nucleic acid differences relevant for a single gene or a limited set of genes.

Of particular interest to the invention are those differential libraries that are built from an initial sample where polynucleotides of different origins were mixed. Preferably encompassed by the invention are those differential libraries, wherein polynucleotides from two different situations (e.g. healthy vs pathologic, apoptotic vs non apoptotic, etc) were mixed to obtain the initial polynucleotide sample. Libraries obtained with such initial samples are thus enriched in polynucleotides characteristic of the nucleic acid differences existing between both situations.

Another object of the invention relates to the polynucleotides isolated by any of the method of the invention regardless of whether they have been cloned or not. In one embodiment, the invention relates to compositions comprising related polynucleotides isolated by any method of the invention, wherein said polynucleotide sequence comprises, consist essentially of or consist in nucleic acid differences. In a preferred embodiment, the invention relates to compositions comprising related polynucleotides isolated by any method of the invention, wherein said polynucleotide sequence comprises, consist essentially of or consist in alternative splicing events. In another embodiment, the invention relates to compositions comprising related polynucleotides isolated by any method of the invention, wherein said polynucleotide sequence comprises, consist essentially of or consist in nucleic acid differences, preferably alternative splicing events, representative of a given situation or environment. In a second more preferred embodiment the invention relates to compositions comprising related polynucleotides isolated by any method of the invention, wherein said polynucleotide sequence comprises, consist essentially of or consist in nucleic acid differences, preferably alternative splicing events, present in one test situation and absent from a reference situation.

Encompassed by the invention are also fragments of polynucleotides isolated by any method of the invention. Preferred fragments are those comprising, consisting essentially or consisting of a nucleic acid difference. Other preferred fragments are those that may be used as primers and probes to detect a nucleic acid difference. Design of such primers and probes are described further below.

Any of the polynucleotides, or fragments thereof, isolated using any method of the invention, as well as primers and probes designed to detect nucleic acid differences identified using any method of the invention, may be conveniently immobilized on a solid support. The solid support is not critical and can be selected by one skilled in the art. Thus, latex particles, microparticles, magnetic beads, non-magnetic beads (including polystyrene beads), membranes (including nitrocellulose strips), plastic tubes, walls of microtiter wells, glass or silicon chips, sheep (or other suitable animal's) red blood cells and duracytes are all suitable examples. Of particular interest are arrays containing any polynucleotide, primer or probe, of the present invention, or sets thereof.

Identification of Differences

Optionally, related polynucleotides harboring nucleic acid differences may be subjected to a step of identification. Preferably, such polynucleotides are first cloned into an appropriate vector, replicated in a host cell, and isolated in order to obtain individual clones that could be maintained in culture.

Analysis of nucleic acid differences may be performed by several method known to those skilled in the art including those described in Myers et al., Nature 313:495, 1985; Cotton et al., Proc. Natl. Acad. Sci. USA 85:4397, 1988; Myers et al., Science 230:1242, 1985; Orita et al., Proc. Natl. Acad. Sci. USA 86:2766, 1989, each of which is incorporated herein by reference in its entirety. The preferred method to identify nucleic acid differences is direct sequencing. DNA sequencing is a routine procedure, and many protocols and reagents are readily available in the art (see, for example, Sequenase Kit from United States Biochemical, Cleveland, Ohio, 1994/95 Catalog #70770, #71350, and #70700).

Preferably, once the nucleic acid differences have been identified, it is generally worthwhile to clone the corresponding polynucleotide(s) (or a portion thereof) from the initial sample(s) in order to confirm that the nucleic acid differences are in fact present at the appropriate location and are not the result of experimental artifacts introduced when carrying out the methods of the invention.

Also, it is generally valuable to search available genetic sequence databases (such as, for example, GenBank, EMBL, DDBJ) to determine whether the identified nucleic acid differences occur on genes that are already known. Alternatively, the present invention allows the identification of at least a partial sequence of an unknown or partially known gene containing the identified nucleic acid differences. Techniques are readily available in the art that allow cloning of a complete gene once partial sequence has been identified (see, for example, Sambrook et al. supra, Chapters 8 and 9; Klickstein et al. Current Protocols in Molecular Biology, Ausubel et al, eds, John Wiley & Sons, New York, N.Y., 1995, Chapter 5, each of which is incorporated herein by reference in its entirety).

When related polynucleotides are isolated from a sample resulting from the mixing of samples of at least two different sources, environments or physiological situations, as in the case of differential libraries, nucleic acid differences existing in one or more initial samples may be distinguished from nucleic acid differences resulting from the actual differences between situations as follows. Detection of polynucleotides harboring identified nucleic acid differences present in each initial sample is conducted in parallel with detection of polynucleotides harboring identified nucleic acid differences present in the mixed sample using primers or probes that are specific for said identified nucleic acid difference. Nucleic acid differences specific to the differences between initial samples will be detected only in the mixed sample whereas other nucleic acid differences will be detected in other samples. Such detection may be conducted using any technique known to those skilled in the art including hybridization-based methods and amplification-based methods.

In a preferred embodiment, polynucleotides from each sample (all initial sample and the mixed sample) are spotted on any convenient solid support, for example a filter, a membrane or a biochip using any techniques known to those skilled in the art. Then, those arrayed polynucleotides are hybridized independently with several oligonucleotide probes binding to the different identified nucleic acid difference. Preferably, one pair of oligonucleotide probes per nucleic acid difference to analyze is used. Preferably, pairs of oligonucleotide probes are designed in order to be specific for a specific polynucleotide. For example, one probe of a pair may be specific for the presence of a particular region that is alternatively spliced, whereas the other one may be specific for the exclusion the same region. Further direction to the design of primers and probes are given below.

Using this method, it is thus possible to determine whether the nucleic acid difference identified exists in a sample from a given source, environment or physiological situation or whether it exists only in the mixed sample. Nucleic acid differences existing only in the mixed sample are due to the differences existing between the sources, environments or physiological situations considered. In addition, such detection also allows to measure and compare the relative proportions of the related polynucleotide species in different sources, environments or physiological situations. Such comparison will reveal not only the presence or absence of some polynucleotide species in some situations (qualitative change) but also an eventual change in the splicing profile (quantitative change).

Kits

Also encompassed by the invention are kits for performing any of the methods of the invention. Indeed, the invention encompasses kits for the isolation of polynucleotides harboring nucleic acid difference in a polynucleotide sample, said kits comprising a) reagents for the annealing of polynucleotides in said sample;
b) a Recognition Element having a preferential affinity to single stranded polynucleotides compared to double stranded polynucleotides; and
c) reagents for the selection of ISSRHs using said RE.

Said reagents for the annealing of polynucleotides may be any of the reagents known to those skilled in the art, preferably any of the ones cited herein. More preferably, said reagents may be any buffer or solvents known to promote annealing of single stranded polynucleotides.

In one embodiment, said RE is an antibody, preferably an autoantibody able to bind preferentially to single stranded DNA molecules. In another embodiment, said RE is a peptide. In still another embodiment, said RE is a protein. More preferably, said RE is a single strand binding protein (SSB). Even more preferably, said RE is selected from the group consisting of the $E.\ coli.$ SSB, the product of gene 32 of phage T4, the adenovirus DBP and the calf thymus UP1. Even more preferably, said RE is the $E.\ coli.$ SSB. In still another embodiment, said RE is a material selected from the group consisting of benzoylated-naphthoylated-DEAE-cellulose (BNDC), methylated albumin on bentonite (MAB) and methylated albumin on Kieselgur (MAK). More preferably, said RE is BNDC.

Said reagents for the selection step comprise reagents allowing said RE to bind to ISSRHs and allowing separation of ISSRH-RE complexes from said polynucleotide sample. Such reagents will be obvious to one skilled in the art once the RE to use in said selection step is determined and once the operating procedure to allow binding and separation are determined. Examples of reagents to use are given in the section entitled "Single stranded trap" and in the Example section. For example, if the RE is a protein, said reagents may comprise a binding buffer and any means to separate protein-nucleic acid complexes from uncomplexed nucleic acids including but not limited to nitrocellulose filters and phenol chloroform. Alternatively, if an His-tagged SSB is used, said reagents comprise the affinity matrix, such as a Ni-NTA His*Bind resin, to which the tagged protein will bind as well as the binding, washing and elution buffers. Alternatively, if said RE is a material usable as a column, said reagents comprise washing, binding and elution buffers.

Optionally, said kit comprises reduction reagents to reduce the size of polynucleotides, preferably by fragmentation, more preferably to a size suitable for single pass DNA sequencing. In a preferred embodiment, said reduction reagents comprise a fragmentation enzyme able to fragment polynucleotides as well as buffer to perform such digestion. In more preferred embodiments, said enzyme is DNase I. In another preferred embodiment, said enzyme is an endonuclease, preferably a restriction endonuclease.

Optionally, said kit comprises denaturation reagents. Such denaturation reagents may be buffers with a low ionic strength, an acidic or alkaline pH, and/or certain solvents such as fornamide or urea.

Optionally, said kit comprises cleaning reagents to remove single-stranded regions other than internal single-stranded regions on ISSRHs. In one preferred embodiment, said cleaning reagents comprise an exonuclease able to digest single stranded nucleic acid molecules including single stranded free ends of double stranded polynucleotides but not internal single stranded regions, as well as a buffer to perform such digestion. In a more preferred embodiment, said exonuclease is exonuclease VII.

Optionally, said kit comprises blunting reagents to blunt polynucleotides obtained after step (b). Preferably, such blunting reagents comprise DNA polymerases exhibiting both a 3'→5' exonuclease activity and a 5'→3' DNA polymerase activity, as well as a buffer to perform such blunting. In one preferred embodiment, said DNA polymerase is the T4 DNA polymerase or the Klenow fragment of $E.\ coli$ DNA polymerase I Optionally, said kit comprises ligating reagents to ligate an oligonucleotide adapter to polynucleotide ends. Such ligating reagents comprise an oligonucleotide adapter designed as described herein, a ligase as well as a buffer to perform ligation. Preferably, said oligonucleotide adapter comprises at least one restriction enzyme site, preferably at least one rare restriction site. Preferably, said ligase is T4 DNA ligase. Optionally, said kit also comprises adapter removal reagents to remove said ligated adapter. Preferably, said adapter removal reagents comprise a restriction enzyme for said restriction site as well as a buffer to perform such digestion.

Optionally, said kit comprises amplifying reagents to amplify ISSRHs selected by said single stranded trap. Preferably, such amplifying reagents comprise a thermostable DNA polymerase and a buffer to perform PCR. Optionally, said amplifying reagents also comprise primers able to hybridize to isolated polynucleotides. Preferably, such primers are able to hybridize to said ligated adapter and are suitable to be used in PCR.

Application

The method according to the invention may be used to identify nucleic acid differences existing between related polynucleotides originating from a single gene or a limited set of genes and representative of a given situation, using a polynucleotide sample targeted for said single gene or limited set of genes, and from a single situation. For example all splicing isoforms (or all splicing events if the targeted cDNA sample was reduced) for said gene or said limited set of genes may be isolated in a given situation such as a tissue of interest. In another example, different alleles (or, preferably, nucleic acid differences between such alleles if the targeted DNA sample was reduced) of a gene or limited set of genes, such as candidate genes for a disease, may be isolated in a given situation, such as a given diseased state.

Originating from a single gene or from a limited set of genes and representative of different situations, using a polynucleotide sample targeted for said single gene or said limited set of genes but resulting from the mixing of samples from different origins. Such an approach is particularly useful to compare related polynucleotides from two or more different situations such as a control vs an experimental sample, a diseased vs a healthy sample, a tissue-specific sample vs other tissue specific samples. For example, related polynucleotides (or, preferably, nucleic acid differences if the targeted polynucleotide sample was reduced) for a given gene or limited set of genes, for example candidate genes for a given disease, may be isolated in a patient vs a healthy person by mixing complex DNA samples originating from both individuals and then carrying out a targeting step as above described.

Representative of a given situation, using a complex polynucleotide sample from a single situation. For example, all isoforms corresponding to transcripts subjected to alternative splicing event (or all alternative splicing events if the cDNA sample was reduced) representative of a given situation may be isolated.

Representative of different sources, origins or situations, using a complex polynucleotide sample resulting from the mixing of samples from different origins. Such an approach is particularly useful to compare related polynucleotides from two or more different sources, origins or situations such as a control vs an experimental sample, a diseased vs a healthy sample, a tissue-specific sample vs other tissue specific samples etc. For example, all isoforms corresponding to transcripts subjected to alternative splicing event (or all alternative splicing events if the cDNA sample was reduced) may be isolated in a control vs a experimental person by mixing complex DNA samples originating from both individuals. As another example, genomic DNA differences between two bacterial strains may be identified by mixing the two different genomic DNA and then applying the methods of the invention.

One of the advantage of these techniques is to isolate not only the nucleic acid differences but also the flanking sequences (when the reduction step is performed) and even the corresponding full length polynucleotides (when the reduction step is not performed). Therefore, once identified, knowledge of the differences and of flanking sequences allow the design of oligonucleotides that may be specific for the nucleic acid differences. In addition, such nucleic acid differences may appear to be specific of a given environment or specific of the differences between diverse situations, thus allowing the design of oligonucleotides not only specific for the nucleic acid difference but also specific for said environment or difference between environments.

Such oligonucleotides that are specific for a nucleic acid difference, and eventually also specific of a given situation or difference between situations, may then be used in screening and diagnostic assays to detect whether the nucleic acid difference is present in a sample to be tested, and eventually whether the sample originates from a specific situation. They may also be used as an antisense tool for gene therapy approaches.

Polypeptide Expression

Polynucleotides containing nucleic acid differences according to the invention, or fragments thereof, preferably cDNAs that were not subjected to a reduction step, may be used to express the polypeptide they encode or part thereof. Such polynucleotides are cloned in an expression vector and expressed using techniques well known to those skilled in the art. The invention encompasses polypeptides encoded by the polynucleotides comprising nucleic acid differences selected by any of the methods according to the invention. The invention also encompasses polypeptides encoded by fragments of said selected polynucleotides. In addition, the invention encompasses fragments of polypeptides encoded by said selected polynucleotides.

Detection of Polynucleotides Containing Nucleic Acid Differences

Detection of polynucleotides containing nucleic acid differences may be performed using probes or primers specific for said nucleic acid differences using any detection techniques known to those skilled in the art. The nucleic acid sample may comprise nucleic acids obtained from a variety of sources, including genomic DNA, cDNA libraries, RNA, or tissue samples. In some applications, the polynucleotide capable of hybridizing to the labeled specific probe or amplified using specific primers may be cloned into vectors such as expression vectors, sequencing vectors, or in vitro transcription vectors to facilitate the characterization and expression of the detected polynucleotides in the sample.

Preferably, detection of polynucleotides containing nucleic acid differences may be performed using one or several specific hybridization probe using any hybridization techniques known to those skilled in the art. Procedures used to detect the presence of nucleic acids capable of hybridizing to said probe include well known techniques such as Southern blotting, Northern blotting, dot blotting, colony hybridization, and plaque hybridization. For example, a nucleic acid sample to be tested containing a sequence capable of hybridizing to the labeled probe is contacted with the labeled probe. If the nucleic acid in the sample is double stranded, it may be denatured prior to contacting it with the probe. In some applications, the nucleic acid sample may be immobilized on a surface such as a nitrocellulose or nylon membrane. Preferably, said hybridization is carried out under stringent conditions. Sets of stringent conditions are well known in the art.

Alternatively, any amplification method known to those skilled in the art may be used to detect specific nucleic acid differences on polynucleotides present in a sample including, those described herein in the section entitled "Preparation of targeted polynucleotide samples". The PCR technology is the preferred amplification technique used in the present invention.

Generation of Primers and Probes

Design of primers and probes is well known to the man skilled in the art taking into account the melting temperature of the probe, length of the primer or probe, the ionic strength of the solution and the G+C content (usually between 10 and 75%, preferably between 35 and 60%, and more preferably between 40 and 55%). Such primers and probes are 8 generally to 1000 nucleotide long, preferably 10 to 100 nucleotide long, more preferably 15 to 30 nucleotide long. For amplification purposes, pairs of primers with approximately the same Tm are preferable. Primers may be designed using the OSP software (Hillier and Green (1991) PCR Methods Appl., 1: 124–8), the disclosure of which is incorporated by reference in its entirety, based on GC content and melting temperatures of oligonucleotides, or using PC-Rare (http://bioinformatics.weizmann.ac.il/software/PC-Rare/doc/manuel.html) based on the octamer frequency disparity method (Griffais et al., 1991), the disclosure of which is incorporated by reference in its entirety.

Figure 2:
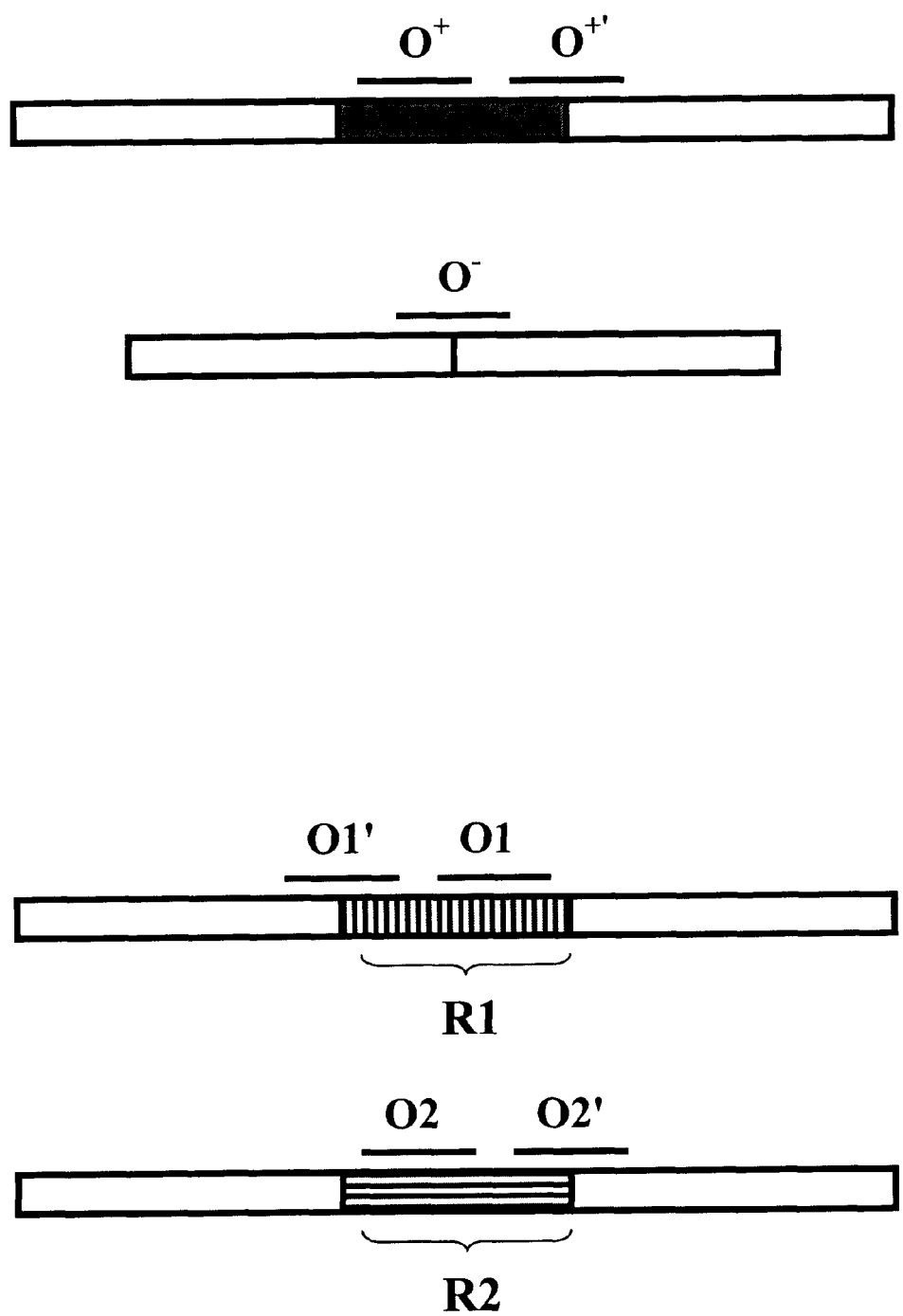
FIG. 2 is an illustration of the choice of probes specific for a nucleic acid difference. Regions identical in related polynucleotides are open boxes. Oligonucleotide probes are represented by black thick lines and are localized with respect to related polynucleotides harboring a nucleic acid difference.

Probes specific of nucleic acid differences may be designed as follows. If the nucleic acid difference consists in addition or deletion of a region, the probe may be designed to bind exclusively to said region (probe O⁺ on FIG. 2a), to the junction region between said region and one of the 5' or 3' adjacent region (probe O⁺' on FIG. 2a), or to the junction between the region 5' and 3' adjacent to said regions that are joined together when said region is deleted (probe O⁻ on FIG. 2a). Probes of the first and second types allow the detection of the polynucleotide containing said region (splicing isoform with the alternative exon, genomic regions with an insertion or with an extension repeat) whereas probes of the third type allows the detection of the polynucleotides in which said region is absent (splicing isoform without the alternatively spliced exon, genomic regions without any insertion or with a deletion).

If the nucleic acid difference consists in replacement of a region (R1) by another (R2) region, as is the case in alternative splicing when two or more exons are alternatively used at a given location on a transcript, the probe may be designed to bind exclusively to either R1 or R2 regions (probe O1 or O2 on FIG. 2b), or to the junction region between either R1 or R2 regions and one of the 5' or 3' adjacent regions (probe O1' or O2' on FIG. 2b).

Primers specific of nucleic acid differences may be designed as follows. If the nucleic acid difference consists in addition or deletion of a region, the primers may be designed to bind to the adjacent regions of said region. The obtained amplification product of a polynucleotide containing said region will be longer than the amplification product of a polynucleotide in which said region is not present. Thus, the size of the amplicon will allow to determine whether a given exon is present or absent.

If the nucleic acid difference consists in replacement of a region (R1) by another (R2) region, as is the case in alternative splicing when two or more exons are alternatively used at a given location on a transcript, the primers may be designed to bind to the 5' and 3' adjacent regions of said region. Provided the length of the alternatively used exons are different, the size of the amplicon will allow to determine which exon is present. Alternatively, at least one of the primers may be designed to bind specifically to the junction region between either R1 or R2 and one of their 5' or 3' adjacent region. In this case, it is the presence or absence of an amplicon that will allow to determine which exon is present or absent.

It will be apparent to one skilled in the art that other types of primers and probes may be designed to detect nucleic acid differences on a case by case basis.

Any of the polynucleotides of the present invention, including primers and probes, may be labeled, if desired, by incorporating any label known in the art to be detectable by spectroscopic, photochemical, biochemical, immunochemical, or chemical means. The detectable polynucleotide may be single stranded or double stranded and may be made using techniques known in the art, including in vitro transcription, nick translation, or kinase reactions.

In a particular embodiment of the invention, a set of primers or probes may be generated based on polynucleotides containing nucleic acid differences representative of a given environment (e.g. specific expression in a given tissue/cell/organelle, expression at a given stage of development or of a process such as embryo development or disease development). Such primers or probes may be used as markers for a specific context. Therefore, the invention encompasses uses of the polynucleotides of the invention as context markers.

Such primers and probes are useful commercially to identify samples of unknown origin, for example, forensic samples, differentiated tumor tissue that has metastasized to foreign bodily sites, or to differentiate different tissue types in a tissue cross-section using any technique known to those skilled in the art including in situ PCR or immunochemistry for example. The primers and probes of the present invention may be used in methods of determining the identity of an unknown environment. As part of determining the identity of an unknown environment, the polynucleotides of the present invention may be used to determine what the unknown environment is and what the unknown sample is not.

Such primers may also be useful in diagnostic application when the set of probes or primers used is specific for a given disease or disorder. When several sets of probes are available for different stages of a given disease, such probes may also be useful to follow the evolution of said disease and the effect of an eventual treatment. Hence, such sets of primers and probes may be useful to test molecules of pharmacological interest. Thus the invention also relates to the identification of molecules of therapeutic or diagnostic interest.

Such primers and probes may also be useful in the context of the identification of pathogen resistance to a given drug. Indeed, if the acquisition by a given pathogen of a sudden resistance to a given drug is caused by the deletion or to an acquisition of a new sequence in the genome, primers and probes of the invention may be used to detect such resistance of a pathogen identified in a given individual in order to give said individual an appropriate treatment.

In addition, sets of primers and probes specific for the detection of a large number of alternative splicing events may be useful to test molecules able to affect the splicing machinery by monitoring those alternative splicing events in a test situation compared to a control situation.

Quantification of mRNA Isoforms Using Arrays

Nucleic acid differences identified using any method of the invention may allow the design of oligonucleotide probes that may be used to measure the relative proportions of related polynucleotides harboring such nucleic acid differences. For example, the relative proportions of different isoforms may be determined using primers specific for the different alternative splicing events identified using any method of the invention. Oligonucleotide arrays for such determination may be prepared as follows.

1) For each alternative splicing event identified by the methods of the invention, a pair of oligonucleotide is designed, the first oligonucleotide of a pair being specific for one isoform (e.g. an oligonucleotide comprising an exon or part of an exon that is alternatively spliced) and the second oligonucleotide being specific for the other isoform (e.g. an oligonucleotide not comprising said exon or part of said exon that is alternatively spliced). For more specific details on the design of such oligonucleotides, see FIG. 2 and the section entitled "Generation of primers and probes".

2) The different couples of oligonucleotides specific for a given isoform are then arrayed on any appropriate support (macroarrays or microarrays).

3) Such arrays may then be hybridized with different probes characteristic of a given source, environment or physiological situation to analyze. Such characteristic probes may be obtained by reverse transcription of mRNAs isolated from said source, environment or physiological situation to analyze, thus yielding a complex single stranded cDNA probe.

4) The relative proportions of each isoform is measured by the ratio of the signal intensity of each oligonucleotide pair. Such ratio is determined for each pair. The sets of such ratios is characteristic of said situation to analyze. Such sets of ratios are determined for each sources, environments or physiological situations to analyze and then compared.

Such arrays, referred to herein as "isoform monitoring arrays", will be precious tools in various applications such as: the identification of genes responsible for various pathologies, the identification of genes involved in a signaling pathway, in a given biological process or in a physiological response to a given stimuli, the identification of markers for prognostic or diagnostic purposes, the prediction or improvement of the therapeutic potential of test compounds (genopharmacology), pharmacogenomics, the classification of tumors, etc.

Use in Genopharmacology

The aim is to evaluate the protective effect of a test compound in a pathological situation. For example, let's review how to determine the neuroprotective effect of a test compound using a cellular model in which cells are able to mimic some neurodegenerative aspects. For example, following a given treatment T, these cells become apoptotic. The neuroprotective effect of said compound may be determined as follows:

1) Alternative splicing events for a limited set of genes, those known to be involved in apoptosis, are identified using an appropriate targeted cDNA sample in which samples from stimulated cells (pathologic situation) and non treated cells (normal situation) are mixed.
2) Isoform monitoring arrays specific for the identified nucleic acid differences are prepared as above described and then hybridized with complex cDNA probes characteristic for the different situations: i) non treated cells, ii) stimulated cells and iii) stimulated and treated cells.
3) Sets of ratios of splicing isoforms are determined in each of the three situations. The neuroprotective effect of the test compound will be assessed by its capacity to produce ratios away from the pathologic situation and close to the normal situation.

Use in Tumor Classification

Pathologists and clinicians in charge of the management of patients with cancer are facing two major problems, namely the extensive heterogeneity of the disease and the lack of factors—among conventional histological and clinical features—predicting with reliability the evolution of the disease and its sensitivity to cancer therapies. For example, breast tumors of the same apparent prognostic type vary widely in their responsiveness to therapy and consequent survival of the patient. New prognostic and predictive factors are needed to allow an individualization of therapy for each patient. Arrays of oligonucleotides able to monitor the modifications that take place in human tumor at the level of splicing will be extremely useful for classifying a heterogeneous cancer into tumor subtypes with more homogeneous clinical outcomes, and to identify new potential prognostic and predictive factors. Such arrays may be designed as follows:

1) Alternative splicing events for a limited set of genes, those known to be involved in cancer, for example in breast cancer, are identified using an appropriate targeted cDNA sample in which samples from different breast cancerous patients are mixed.
2) Isoform monitoring arrays specific for the identified nucleic acid differences are prepared as above described and then hybridized with complex cDNA probes, each being characteristic of a given cancerous patient. Thus, sets of isoform ratios are obtained that are characteristic for each patient.

Provided the clinical status of each patient is well defined, splicing profiles characteristic of different cancerous situations (such as different types of breast cancer, different stages of a given cancer, . . . ) are obtained. For example, analyses of such profiles allow to distinguish in a group apparently homogenous, different subgroups of patients with different clinical parameters (absence of metastasis in one group compared to another, differences in response to a given treatment, etc). In addition, comparison of such profiles with a profile obtained for a non classified patient may help in the diagnosis and prognosis specific to said non classified patient.

Screening

Polynucleotides containing nucleic acid differences according to the invention, especially primers or probes designed to be specific of a difference as described above, may be used to screen genomic or cDNA libraries using any technique known to those skilled in the art (see Sambrook et al. supra, Chapters 8 and 9, incorporated herein by reference in its entirety) including those mentioned below. For example, if a nucleic acid difference has been identified on a reduced sample, the full-length polynucleotides containing such nucleic acid difference may be retrieved by screening libraries, preferably libraries containing mostly full-length polynucleotides using primers and probes specific for said difference. In another example, if a defined region thought to exert a specific function, although not necessarily a known function, (e.g. a functional domain) was shown to be alternatively spliced under given circumstances, primers and probes specific for this domain may be used to retrieve polynucleotides encoding polypeptides with similar domains, preferably polynucleotides encoding polypeptides belonging to the same protein family. As is known in the art, effective library screening requires stringent hybridization conditions. Many suitable sets of stringent hybridization conditions are well known in the art (see, for example, Sambrook et al. supra Chapter 8).

Antisense

Polynucleotides comprising alternative splicing events are cloned in order to allow transcription from the opposite strand with respect to the stand normally transcribed in the cell. Libraries according to this embodiment are called antisense libraries. They contain antisense polynucleotides able to alter the expression of a given gene, and may even be specific for a given splicing isoform. Such an antisense library may then be transfected in cells of interest and the alteration of a given phenotype be studied. Analyses of phenotypic variations following such transfections are usually performed upon the selection of clones having stably integrated the expression vector. The major advantage of using such antisense libraries is the ability to identify not only the gene which expression has been altered yielding a selected phenotype but also to identify which splicing isoform has been affected. The invention encompasses antisense libraries generated with the polynucleotides comprising the alternative splicing events.

The invention also encompasses the antisense polynucleotides having a complementary sequence to the polynucleotides comprising the alternative splicing events as single species. Preferably, such an antisense polynucleotide comprises a sequence complementary to a given splicing isoform. More preferably, such an antisense polynucleotide comprises a sequence complementary either to an exon which is alternatively spliced or to at least one of the junctions between said alternatively spliced exons and an adjacent exon. Such antisense polynucleotide will be specific for the isoform containing said alternatively spliced exon. Alternatively, such an antisense polynucleotide comprises a sequence complementary to the junctions between flanking exons when the alternatively spliced exon is absent. Such antisense polynucleotide will be specific for the isoform not containing said alternatively spliced exon. Such antisense polynucleotides or the vectors convenient for the expression of said antisense polynucleotide may be used to modify the expression of the corresponding gene, preferably to modify the expression of one or several alternatively spliced mRNAs of said gene, more preferably to inhibit said expression. Such antisense polynucleotide or vectors may also be used to modify the alternative splicing profile of one gene by decreasing the expression of a given splicing isoform or by inhibiting splicing. Strategies for designing antisense polynucleotides suitable for use in gene therapy are well known to those skilled in the art including, for example, techniques described in WO 95/24223, in Sczakiel G. et al. (1995 Trends Microbiol. 3(6):213–217), in Green et al., (Ann. Rev. Biochem. 55:569–597 1986) and Izant and Weintraub, (Cell 1984 Apr;36(4):1007–15), and by Rossi et al.(Pharmacol. Ther. 50:245–254, (1991)), the disclosures of which are incorporated herein by reference in their entireties.

EXAMPLES

The following examples described particular embodiments of the invention. They are meant as illustrating and not limiting the invention.

Example 1

Single Stranded Trap with the SSB Protein

Figure 3:
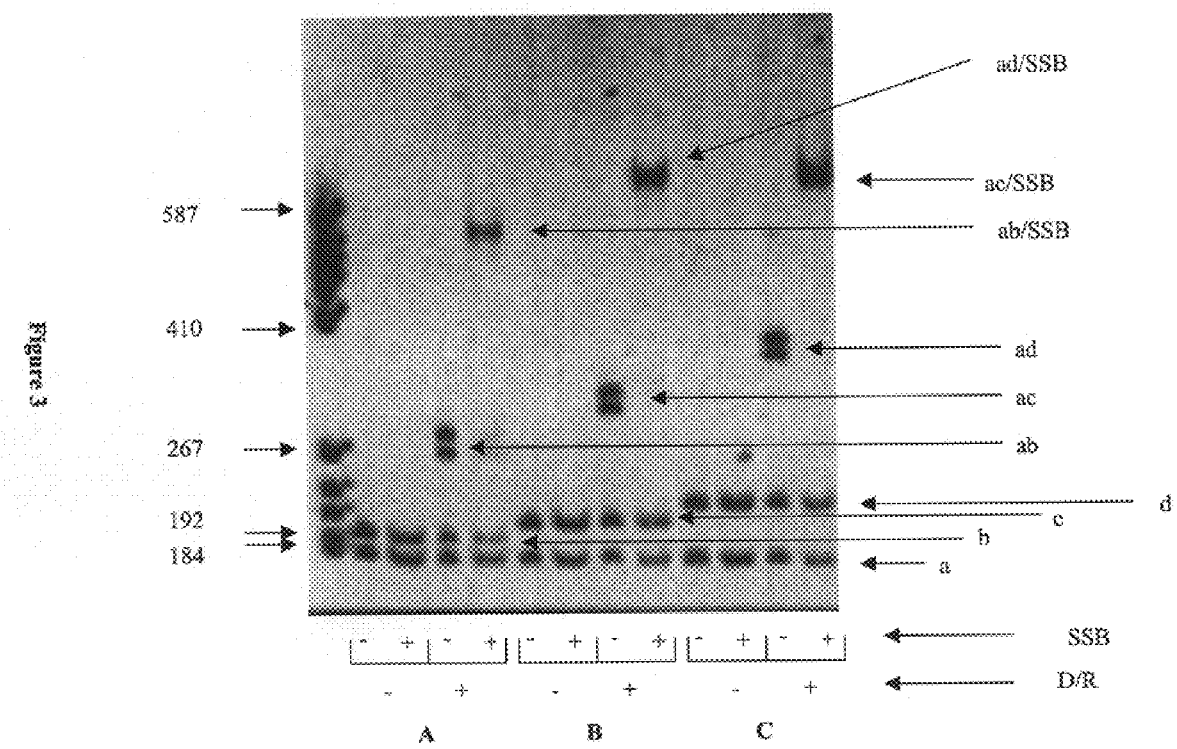
FIG. 3 is a half-tone reproduction of a gel retardation assay showing the efficiency of a single-stranded trap with the E coli SSB protein. Three samples (A, B and C) comprised an equal amount of two polynucleotides, one consisting of a region x adjacent to a region y and the other one consisting of adjacent regions x, z and y. The length of the z region differs between the three samples: in A case, $z1=17$ bp ; in B case, $z2=30$ bp ; and, in C case, $z3=40$ bp. On the line "D/R" which means denaturation/renaturation, "−" means without this step and "+" means with this step. On the SSB line, "− means without any SSB protein and "+" means with SSB protein. Three general kind of molecules were found: the homoduplex molecules ($a=xy$, $b=xz_1y$; $c=xz_2y$; $d=xz_3y$); the heteroduplex molecules (ab, ac et ad) and the ISSRH-SSB complexes (ab/SSB, ac/SSB and ad/SSB).

The preferred recognition element according to the invention is the *E. coli* SSB. The ability of the coli SSB to bind specifically a subset of polynucleotide harboring single-stranded regions was assayed as explained below.
1) Gel Retardation Assay with the SSB Protein
a) Principle A first duplex polynucleotide (the so-called reference polynucleotide) comprising two adjacent regions x and y, where x was a 103 bp long sequence and y was a 74 bp long sequence, was mixed with an equal amount of a second duplex polynucleotide with three adjacent regions in the following order x, z and y, where x and y were identical to sequences in the reference polynucleotide and z was an intervening sequence. The resulting sample was exposed to denaturing conditions so that individual nucleic acid strands were separated from one another. The sample was then exposed to annealing conditions so that individual strands annealed to one another. Two types of polynucleotides were then obtained: 1) the homoduplexes formed by the annealing of fully complementary strands, i.e. either one individual strand of the reference molecule (xy) with the complementary individual strand of the same reference molecule or one individual strand containing the intervening sequence (xzy) with the complementary strand containing the intervening sequence; 2) the heteroduplexes formed by the annealing of non-fully complementary strands, i.e., one individual strand of the reference molecule (xy) with a complementary strand containing the intervening sequence (xzy). The homoduplexes were completely double-stranded polynucleotides whereas the heteroduplexes were duplex molecules harboring an internal single-stranded region, namely ISSRHs. Then, the sample comprising homoduplex and heteroduplex molecules was mixed with the *E. coli* SSB protein. The ability of the coli SSB protein to form stable and specific complexes with the heteroduplex molecules only was analyzed using a gel retardation essay.
b) Experimental Conditions and Results A DNA fragment (F) of about 2000 pb was cloned into a plasmid. A unique SmaI site was present in the middle of this fragment. The plasmid vector containing the insert F was digested by SmaI (no other SmaI site existed in the plasmid vector). Blunted double-stranded DNA fragments of 9, 12, 15, 17, 30, 40, 67, and 150 bp were cloned in the SmaI site of insert F. Nine different constructs were obtained: One construct contained insert F only (i.e. reference xy polynucleotide), and 8 constructs contained insert F with an intervening sequence of 9, 12, 15, 17, 30, 40, 67, and 150 respectively (i.e. polynucleotide with a xzy structure in which the size of z varies from 9 to 150 bp respectively). Two PCR primers were designed in order to amplify a region of about 200 bp surrounding the SmaI site of F. More precisely, the binding site of one primer was situated at about 100 bp from the SmaI site and the binding site of the other primer was located on the other side of the SmaI site, at about 100 bp away from it. Using the two primers described above, 9 polynucleotide were produced by PCR amplification of the 9 above-described constructs. The polynucleotides obtained by amplification of the construct containing only insert F, which is called reference molecule, was about 200 bp in length and centered around the SmaI site. The other eight polynucleotide obtained by amplification of the other constructs differed from the reference molecule only by the replacement of the SmaI site by an intervening sequence of 9, 12, 15, 17, 30, 40, 67, and 150 bp respectively. Each of the 8 polynucleotides xzy containing an intervening sequence was mixed with an equal amount of the reference polynucleotide xy, denatured/renatured and incubated with the *E. coli* SSB as described below. The results obtained for three of them are presented in FIG. 3.
Experiment A: z=17 bp Five hundred ng of the reference molecule xy were incubated 15 min at 40 degree Celsius with 500 ng of the $xz_1y$ molecule in 30 microliters of a buffer containing 50 mM sodium acetate (pH 4, 5 at 25 degree Celsius), 280 mM NaCl and 4,5mM ZnSO4. Half of the resulting sample (15 microliters) was then incubated at 37 degree Celsius for 15 min and then loaded on a 4% acrylamide gel (Line 1). The other half was mixed with 6 micrograms of *E. coli* SSB, incubated at 37 degree Celsius for 15 min and loaded on the gel (Line 2).

In lane 1, two bands, (a) and (b), can be seen, where (a) corresponds to the xy homoduplex molecule and (b) to the $xz_1y$ homoduplex molecule. Exactly the same pattern was observed in lane 2. From this observation, it can be concluded that the SSB is not able to form a stable complex with any of the two homoduplex molecules.

Five hundred ng of the xy molecule were mixed with 500 ng of the $xz_1y$ molecule in a final volume of 27 microliters $H_2O$. The sample was incubated 2 min at 98 degree Celsius for denaturation and then incubated at 40 degree Celsius. Then, 3 microliters of a 10×annealing buffer [500 mM sodium acetate (pH 4,5 at 25 degree Celsius), 2,8 M NaCl and 45 mM ZnSO4 ] was immediately added and the resulting sample was incubated 15 min at 40 degree Celsius for annealing. Then, half of the solution (15 microliters) was incubated at 37 degree Celsius for 15 min and then loaded on a 4% acrylamide gel (Line 3). The other half was mixed with 6 micrograms of *E. coli* SSB, incubated at 37 degree Celsius for 15 min and loaded on the gel (Line 4).

When compared to lane 1, we can observe in lane 3 the appearance of additional bands (ab) that migrate slower than (a) and (b). As explained above, these new forms correspond to the heteroduplex molecules produced as the result of the denaturation/annealing step. In lane 4, these additional bands (ab) corresponding to the heteroduplex molecules disappear whereas a new band appears which is strongly retarded and corresponds to the ISSRH-RE complex formed between the (ab) heteroduplex and the SSB protein. From this observation, it can be concluded that the SSB is able to form a stable complex with a duplex structure harboring an internal single-stranded loop of 17 nucleotides.

Experiments B and C: z=30 or 40 bp

For these experiments, the same experimental conditions as in experiment A were used. The only difference is that in B, the intervening sequence $z_2$ was a 30 bp long sequence whereas in C, the length of $Z_3$ was 40 bp. The observed profiles were the same in B and C than in A. This means that, not surprisingly, the SSB is able to form a stable and specific complex with polynucleotide harboring single-stranded loop of 30 and 40 nucleotides.

2) Detection Limit of the SSB Single-stranded Trap

A strong shift was observed for heteroduplexes harboring single-stranded loops of 15, 17, 30, 40, 67, and 150 nucleotides whereas no shift was observed for the corresponding homoduplex molecules. However, only a small proportion of the heteroduplex containing the loop of 12 nucleotide was retained by the SSB and no shift was observed with the heteroduplex containing the loop of 9 nucleotides.

From these results, we concluded that the E coli SSB protein is able to form a stable and specific complex with polynucleotide harboring single-stranded regions of at least 15 nucleotides. Since very few exons are less than 15 nucleotides long, the E coli SSB protein is a suitable recognition element in a single-stranded trap designed for identifying alternative splicing events.

Example 2

Isolation of All Alternative Splicing Isoforms Found in a Given Condition

Figure 4:
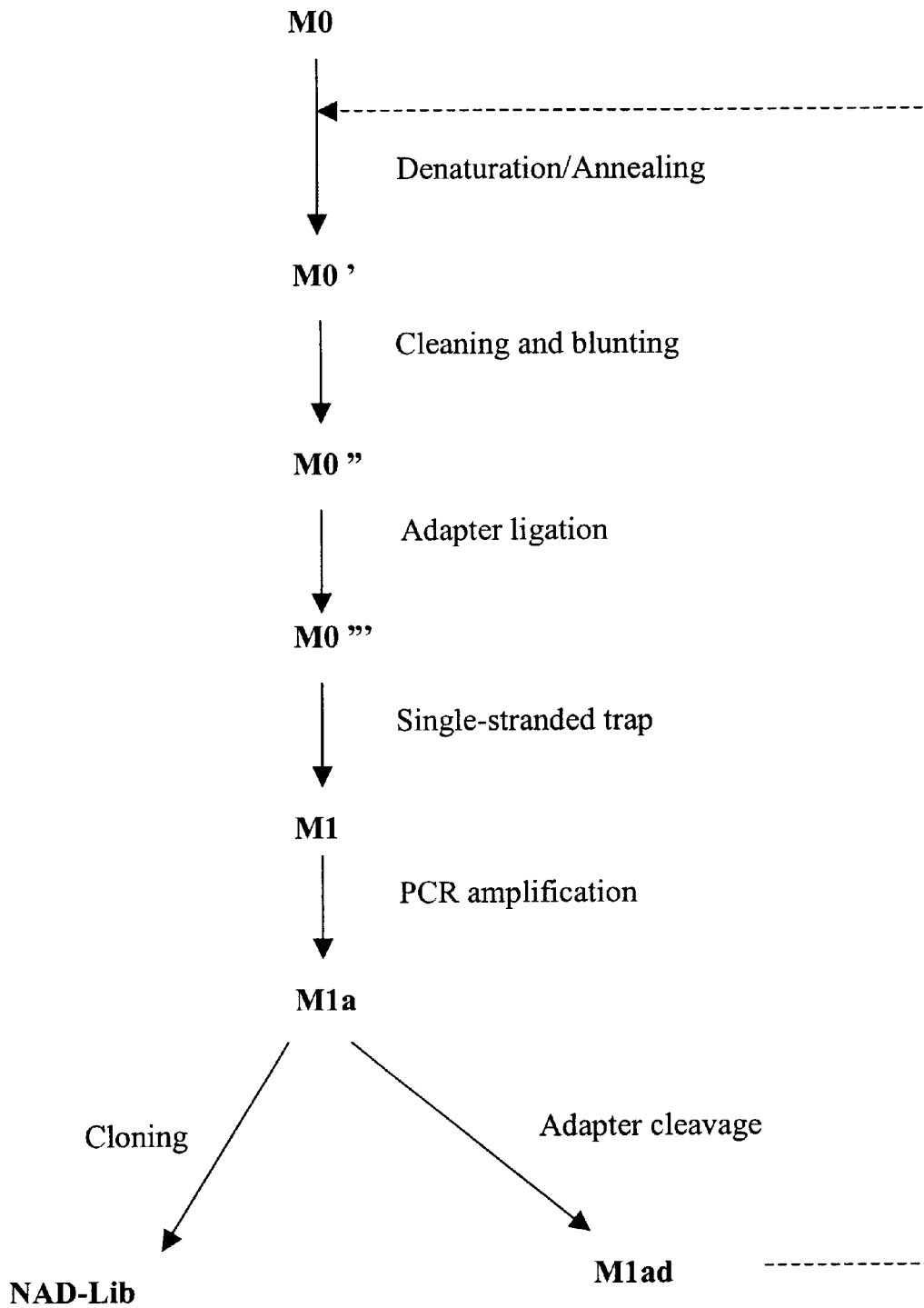
FIG. 4 is a flow chart illustrating several steps of a method for obtaining a library enriched with related polynucleotides harboring nucleic acid differences (NAD-Lib). The dashed line illustrates the enrichment loop that may be reiterated several times if necessary. More information on this method is disclosed in Example 2.

This method allows to identify mRNAs subjected to alternative splicing and to characterize the corresponding alternative splicing events found in a given context. FIG. 4 illustrates this method.

1) Preparation of the Complex cDNA Sample

The initial sample is a sample containing polynucleotides, preferably double stranded cDNAs generated from mRNAs isolated from a source of interest (e.g. a tissue type such as brain). It may alternatively contain single stranded cDNAs, mRNAs, or cDNA-mRNA hybrids. mRNAs are obtained either from commercial source or from one of the numerous methods known by the man skilled in the art. One method of mRNA preparation is described below.

a) Preparation of the mRNA Sample

Total human RNA or polyA+ RNA derived from different tissues are purchased from LABIMO and CLONTECH and used to generate cDNA libraries as described below. The purchased RNA is isolated from cells or tissues using acid guanidium thiocyanate-phenol-chloroform extraction (Chomczyniski and Sacchi, supra). PolyA+ RNA is isolated from total RNA (LABIMO) by two passes of oligo dT chromatography, as described by Aviv and Leder, supra to eliminate ribosomal RNA.

The quality and the integrity of the polyA+ RNAs are examined as follows. Northern blots are hybridized with a probe corresponding to an ubiquitous mRNA, such as elongation factor 1 or elongation factor 2, to ensure that the mRNAs are not degraded. Contamination of the polyA$^+$ RNAs by ribosomal sequences is examined using Northern blots and a probe derived from the sequence of the 28S rRNA. Preparations of mRNAs with less than 5% of rRNAs are subsequently used in library construction. To avoid constructing libraries with RNAs contaminated by exogenous sequences (prokaryotic or fungal), the presence of bacterial 16S ribosomal sequences and of two highly expressed fungal mRNAs is also examined using PCR. Finally, RNA samples containing intact mRNAs and low levels of either endogenous or exogenous contamination are kept for subsequent steps.

b) Preparation of the cDNA Sample

An aliquot of a mRNA sample of interest, e.g. 10 micrograms mRNA, containing intact mRNAs and low levels of endogenous and exogenous contaminants is then used to synthesize the first strand cDNA with a thermostable reverse transcriptase, preferably an AMV reverse transcriptase, and an oligo dT primer which allows the initiation of the reverse transcription from the poly A tail of the mRNAs. In some instances, the oligo dT primer has a 3' degenerate nucleotide in order to initiate synthesis at the 5' end of the poly A tail. After having produced the first strand cDNA, the second strand is synthesized using a cocktail of 3 enzymes, namely Rnase H, E. coli DNA polyrnerase I and E. coli DNA ligase. As RNAse H eliminates the RNA/DNA hybrids obtained after the reverse transcription, E coli DNA polymerase I generates the second cDNA strand. The newly synthesized second cDNA strand is then ligated with the E. coli DNA ligase. When the second strand cDNA synthesis is over, residual RNAs are degraded and the resulting double-stranded cDNA blunted using an enzymatic cocktail comprising Rnase H, the Rnase A, T4 DNA polymerase and E. coli DNA ligase.

The resulting M0 sample comprises double stranded cDNAs derived from mRNAs extracted from the physiological situation of interest.

2) Preparation of a Sample Enriched in Alternative Splicing Isoforms

The enrichment process contains 5 steps, i.e. a denaturation/annealing step, a cleaning/blunting step, an adapter ligation step, a selection step and an amplification step as follows.

a) Formation of Heteroduplexes by Denaturation/Annealing of the M0 Sample

The double-stranded DNA sample M0 is exposed to denaturing conditions (e.g., 2 min at 98 degree Celsius in 10 mM Tris (pH8), 5 mM EDTA) to ensure that all double stranded molecules separate into their single-stranded components. The resulting single-stranded DNA sample is then exposed to annealing conditions (preferably, 12 to 78 h at 30 degree Celsius in a buffer containing 120 mM NaCl, 10 mM Tris (pH8.0), 5 mM EDTA and 50% deionized formamide) so that individual single-stranded molecules anneal to one another. The resulting DNA mixture is then precipitated with ethanol. Let M0' be the new sample obtained after the denaturation/annealing step.

b) Cleaning and Blunting of the Sample M0'

The cleaning and blunting steps are preferably performed with exonuclease VII and phage T4 DNA polymerase, respectively. First, between 0,2 to 5 micrograms of DNA from M0' is incubated with 2 to 10 units of exonuclease VII for 30 min at 42 degree Celsius in 30 mM K phosphate (pH 7,9), 8 mM Na$_2$.EDTA, 10 mM beta-mercaptoethanol. Then, a cleanup of the sample is performed using the MinElute™ Cleanup System from QIAGEN and the resulting DNA molecules are incubated at 12 degree Celsius for 20 min with 2 to 10 units of T4 DNA polymerase in presence of 0,2 mM of each dNTP and in 50 mM Tris-Hcl (pH 8), 50 mM KCl, 5 mM MgCl2, 5 mM DTT, 50 micrograms/ml BSA. Next, a DNA cleanup is performed again with the MinElute™ Cleanup System from QIAGEN. Let M0" be the new sample obtained after the cleaning/blunting step.

c) Ligation of an Oligonucleotide Adapter

This step of the method consists in the ligation of an adapter, preferably a NotI adapter, to the ends of the blunted polynucleotides present in sample M0".

In a preferred embodiment, the NotI adapter is obtained as follow: 3 nmoles of a first synthetic oligonucleotide with the sequence: 5'OH-CCCGCCACGTCCAAGCGGCCGCAG-3'OH (SEQ ID No:1) is mixed with 3 nanomoles of a second oligonucleotide with the sequence: 5'-PO4-CTGCGGCCGCTTGGACGTGGCG-3'OH (SEQ ID No:2) in a volume of 200 microliters in 100 mM NaCl, 10 mM Tris-Hcl (pH8), 1 mM EDTA. The mixture is then placed first at 90 degree Celsius for 2 min and subsequently at 40 degree Celsius for 30 min. The adapter is now ready to use in the ligation reaction.

The ligation reaction is carried out as follow: between 0,1 to 2 micrograms of DNA from M0" and 2 to 10 micrograms of adapter are mixed together with 50 Weiss units of T4 DNA ligase in a final volume of 100 microliters in 66 mM Tris-Hcl (pH8), 6,6 mM MgCl2, 10 mM DDT, 66 mM ATP, 5% PEG 8000. This reaction mixture is then placed at 10 degree Celsius for 5 to 15 hours. At the end of the ligation reaction, a phenol extraction followed by an ethanol precipitation are performed. After ligation of the adapter, the new sample is called M0'''.

d) Selection of the Heteroduplexes Comprising an Internal Single-stranded Region (ISSRHs) with a Single-stranded Tran The sample M0''' is a sample of double-stranded polynucleotides which contains adapters at the ends. This sample comprises essentially two types of molecules, duplexes (fully complementary) and heteroduplexes with one or several internal single-stranded region(s). ISSRHs from the M0''' sample corresponding to alternative splicing events are preferably isolated from the rest of the sample using a single-stranded trap involving a recombinant His-tagged SSB protein of *Escherichia coli*. This His-tagged SSB protein is advantageously produced using the protocol described by Dabrowski and Kur in *Protein Expression and Purification* 16, 96–102 (1999). With the his-tagged SSB protein in hand, the selection of ISSRHs can be done as followed: 1) The M0'''sample is incubated with 5 micrograms of the His-tagged SSB for 30 min at 37 degree Celsius in 10 mM Tris, pH 7.8, 280 mM Sodium Chloride so that His-Tagged SSB/ISSRHs complexes form. 2) The resulting mixture is then applied directly onto a chromatography column packed with the Ni-NTA His*Bind resin from Novagen so that the His-Tagged SSB/ISSRHs complexes bind to the resin. Then, the column is washed two or tree times with a washing buffer (20 mM Sodium Phosphate, 300 mM Sodium Chloride, pH 7.8) and the ISSRHs are then recovered by eluting the column with an Imidazole Elution buffer (20 mM Sodium Phosphate, 500 mM Sodium Chloride, 500 mM Imidazole, pH6). The eluted His-Tagged SSB/ISSRHs complexes are then treated with proteinase K so that the protein fraction of the complexes is disrupted and that the ISSRHs are freed. A phenol extraction is next performed in order to get rid of the proteinase K and the ISSRHs of the resulting deproteinized mixture are then concentrated by ethanol precipitation.

After the single-stranded trap, the sample is enriched with ISSRHs (or nucleic acids with ASEs). This new sample is called M1. Optionally, this selection step involving the single stranded trap of the invention may be reiterated several times to maximize the recovering of ISSLHs, preferably 1 to 3 times.

e) Amplification by PCR of the M1 Sample

After the above selection step, polynucleotides within the M1 sample are amplified by PCR with a primer able to bind to the primer binding site within the adapter that was ligated to both ends of the selected polynucleotides. For example, a primer with the sequence 5'-ACGTCCAAGCGGCCGCAG-3' (SEQ ID No:3) may be used.

Let M1a be the new sample produced by the PCR amplification of M1.

f) Cloning of M1a (Option 1) or Further Enrichment of M1a (Option 2)

After this first enrichment cycle, the polynucleotides exhibiting ASE(s) may be directly cloned (option 1). Alternatively, another round of enrichment may be carried out (option 2).

f1) Option1: Cloning of M1a

Polynucleotides containing ASEs are cloned using any cloning vector prepared with appropriate cohesive or blunt ends and techniques well known to those skilled in the art. The cloned isolated polynucleotides form a library enriched in nucleic acid difference (NAD-Lib), more precisely a library enriched in alternative splicing isoforms (ASI-Lib). Optionally, such polynucleotides may be digested using any of the restriction enzyme sites, such as Not I, present on the adapter present on both ends of the polynucleotides. Such digestion step generates cohesive ends which will facilitates the cloning.

f2) Option 2: Adapter Cleavage

Before carrying out a new round of ASE enrichment consisting of the 5 steps above described (denaturation/annealing; cleaning and blunting, adapter ligation, single-stranded trap, PCR amplification), the adapter present on the DNA molecules of M1 a are advantageously removed by a digestion of the sample using any of the restriction enzyme sites present on the adapter. For another enrichment cycle, the digestion of the adapter is preferable in order to avoid some hybridization problems between adapter sequences, such as NotI. Let M1ad be the new sample obtained after this digestion. Now, M1ad is ready to enter a new round of ASE enrichment starting by the denaturation/annealing step and ending with the PCR amplification step.

Let M2a be the enriched sample obtained after a second round of ASE enrichment. Here again, the enriched polynucleotides of the M2a sample may either be cloned or submitted to a new round of ASE enrichment.

Example 3

Figure 5:
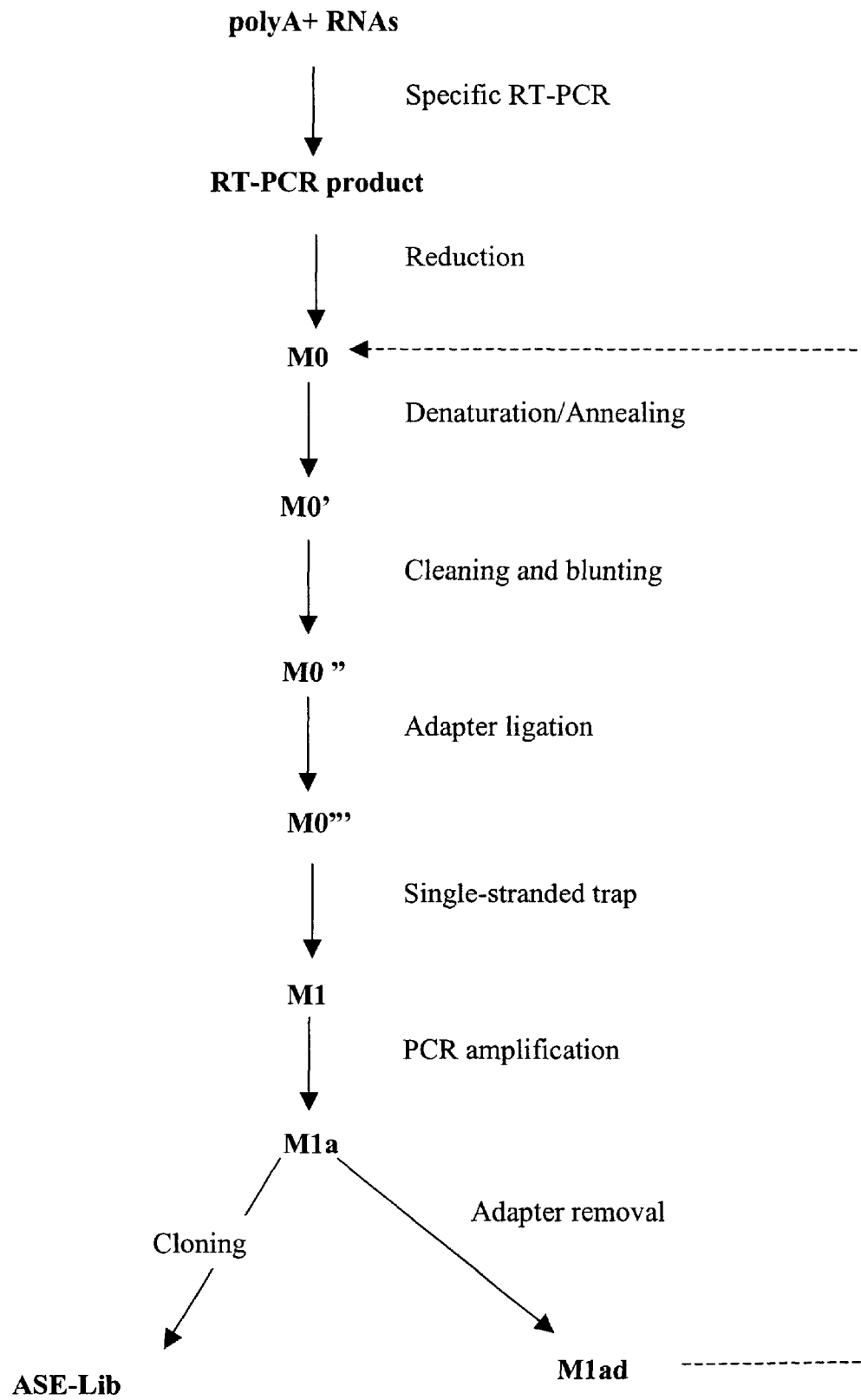
FIG. 5 is a flow chart illustrating several steps of a method for obtaining a library enriched with alternative splicing events for a single gene or a limited set of genes (ASE-Lib). The dashed line illustrates the enrichment loop that may be reiterated several times if necessary. More information on this method is disclosed in Example 3.

Isolation and Identification of Alternative Splicing Events for a Specific Gene in a Given Condition The following protocol provides for the identification of the different splicing isoforms of a specific gene (gene X). The method disclosed in example 3 is illustrated by FIGS. 5 and 6.

1) Preparation of a Targeted Reduced cDNA Sample

The M0 sample is a sample of double-stranded cDNA fragments specific for gene X. It is obtained through RT-PCR followed by fragmentation of the RT-PCR product as follows.

a) Preparation of a Targeted cDNA Sample

In a first step, isolated mRNA or commercially available mRNA are converted into single-stranded cDNAs using any techniques known to those skilled in the art including those described in Example 2.

A small aliquot of the above reverse transcription products is then used as a template in a PCR reaction using primers specific for the gene of interest, namely gene X. Preferably, the primers are designed in order to be able to amplify most of the cDNAs of interest, i.e. the first primer annealing as close as possible to the transcription start site of gene X and the second primer annealing as close as possible to the 3' end of the messenger X, for example in the region corresponding to the polyadenylation site . If the region to amplify is very long, usually more than 6 Kb long, a long-range PCR system is used such as, for example, the Expand™ long template PCR system from Boehringer Mannheim. A sample of double-stranded polynucleotides comprising the different splicing isoforms of X is then obtained.

b) Reduction of the cDNA Sample

Next, a reduction step is performed to obtain fragments of the splicing isoforms of gene X. Preferably, the RT-PCR products are cleaved up to fragments with an average size of about 600 bp using the materials and the conditions of the Dnase Shotgun Cleavage Kit from Novagen. The resulting polynucleotide fragments are then separated by electrophoresis on a 1% to 1.5% agarose gel and the bands corresponding to 200–800 bp are excised. The DNA fragments ranging from 200 to 800 bp are recovered from the agarose band by one of the numerous existing methods well known in the art. Let M0 be the reduced targeted cDNA sample.

2) Preparation of a Library Enriched in Specific ASEs

Enrichment of the M0 sample into ASEs that are specific for gene X and occurring in the original sample(s) of interest is obtained using the same procedure as in the case described in Example 2. Briefly, the fragments specific for gene X are denatured, then renatured. If there are several isoforms of gene X in the M0 sample, duplex polynucleotides harboring internal single-stranded region(s) will be produced each time a strand representing a region subjected to an ASE will anneal to a complementary strand that either lacks an exon(s) or a portion(s) thereof, or has an additional exon(s) or portion thereof. The sample after the annealing step is now called M0'.

Then, the denatured/renatured polynucleotides in the M0' sample are cleaned and blunted. Next, an adapter is ligated to facilitate subsequent amplification and cloning. ISSRHs are then selected using the single stranded trap of the invention. After PCR amplification, polynucleotides containing ASEs are either directly cloned or submitted to another round of enrichment. At the end of the process, a library enriched in short fragments harboring ASEs for gene X (ASE-Lib) is obtained.

3) ASE Identification

Cloned ASEs specific for gene X are then identified as follows. The ASE enriched library is first sequenced and the obtained sequences analyzed for the presence of ASEs using any bio-informatic tools known to those skilled in the art.

Because of the reduction step, the different ASEs of gene X are frequently identified independently from one another because the different ASEs may be present on different isolated polynucleotide species corresponding to the different fragments obtained after the reduction step. Therefore, as soon as at least two independent ASE are identified for a given messenger, the next step is to determine the different isoforms of this gene. For example, 4 different isoforms, namely I1, I2, I3 and I4, may be produced with 2 independent ASEs, i.e. A and B which are 2 ASEs in which an exon or part of an exon is either present or absent, as illustrated in FIG. 6. With these 4 possible isoforms, a total of 11 combinations of these 4 different isoforms in the initial sample are possible. However, out of these 11 possible combinations, only 7 may account for the presence of the 2 ASEs.

The situation becomes far more complicated as the number of ASE increases. To further illustrate, let's take the following example. Assune that gene X is transcribed into a pre-mRNA yielding two splicing isoforms, X1 and X2 of about 3 kb messenger. Further assume that X1 differs from X2 in that: 1) it has an additional exon of 80 nucleotides located in the 5' part of the molecule (first ASE); 2) it lacks two exons, one of 25 nucleotides located in the middle of the molecule (second ASE) and one of 65 nucleotides located in the 3' part of the molecule (third ASE). So, applying the method of the invention, the 3 ASE that characterize gene X will be identified but, due to the reduction step and because these 3 ASE are distant the ones from the others, they will be most probably identified independently. Therefore, one cannot, at this stage, determine what are the different isoforms of gene X. Indeed, the total number of isoforms that can possibly be generated with 3 ASEs is $2^3=8$ and the number of combinations that can account for the 3 ASEs is very high.

Identification of the different isoforms of X may be carried out as follows. In a first step, a library of all the different isoforms of gene X is produced. For example, an RT-PCR is performed as described above and the polynucleotides of the resulting sample are cloned into a vector of interest. Thus, all the different X isoforms will be represented in the library.

In a second step, clones of the library of all the different isoforms of X, preferably 96 to 384 clones of the library, are arrayed on a solid support, for example a filter, a membrane or a biochip using any techniques known to those skilled in the art. Several identical arrayed libraries are produced.

In a third step, the arrayed libraries are hybridized independently with several probes binding to the different identified ASEs of gene X. Preferably, each probe is designed in order to be specific for a given ASE. For example, a probe may be specific for the inclusion of a particular exon that is alternatively spliced if it is hybridizes specifically to part of said exon, or to junctions of said exon with surrounding exons. Alternatively, a probe may be designed to be specific for the exclusion of said exon if it specifically hybridizes to the junctions between exons that are joined together when said exon is spliced out and that surrounds said exon when it is present. Using this method, it is thus possible to determine for each clone of the arrayed library if the different exons that are subject to alternative splicing are present or not and so to infer precisely for each clone what is the corresponding isoform. For example, if two independent ASE have been identified (e.g., ASE1 and ASE2), a first oligonucleotide (oligo 1) can be designed that will recognize the exon sequence that is alternatively spliced in ASE1 (exon 1) and a second oligonucleotide (oligo 2) that will recognize the exon sequence that is alternatively spliced in ASE2 (exon 2). A first hybridization of the arrayed library with oligol is informative of whether exon 1 is present in each clone (a hybridization signal indicate that exon 1 is present, no signal indicate that exon 1 is absent). A second hybridization of the library with oligo 2 is informative of whether exon 2 is present in each clone. So, if a clone hybridizes to oligo 1 but not to oligo 2, this reveals the existence of an isoform in which exon 1 is present and exon 2 is absent. If another clone hybridizes neither with oligo 1 nor oligo 2, this show that an isoform of gene X exists where exon 1 and exon 2 are missing.

Example 4

Isolation and Identification of Splicing Isoforms of a Specific Gene in a Given Condition Different splicing isoforms deriving from a single pre-mRNA in a given situation may be identified as follows.

First, a library enriched in ASE specific of the messenger X is produced as described in the previous example. Then the sequence of the cloned ASEs are identified by sequencing the enriched library. Finally, a library containing the different isoforms of the messenger X is generated using any techniques known to those skilled in the art. Clones from that library are arrayed on a solid support and then hybridized to probes able to bind to the different ASEs of messenger X in order to identify ASE present on each clone and deduce the different X isoforms as described in the previous example.

Figure 7:
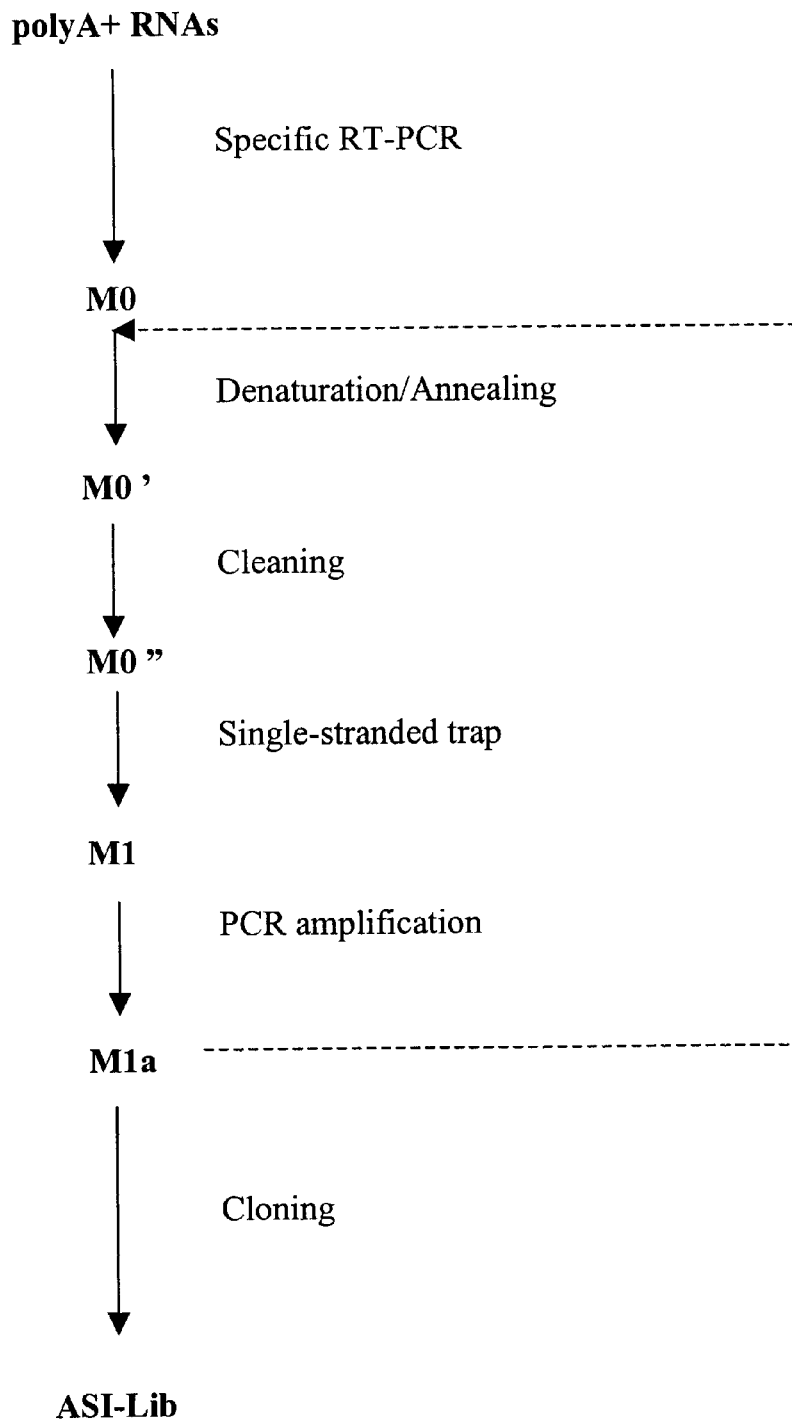
FIG. 7 is a flow chart illustrating several steps of a method for obtaining a library of isoforms for a single gene or limited set of genes (ASI-Lib). The dashed line illustrates the enrichment loop that may be reiterated several times if necessary. More information on this method is disclosed in Example 4.

Alternatively, splicing isoforms of a single gene may be produced using essentially the same procedure as described in Example 3 except that the reduction step is omitted. Therefore, instead of obtaining short fragments containing essentially ASEs and their surrounding sequences after the enrichment loop, this method yields longer polynucleotides containing ASEs, preferably full-length splicing isoforms. A flow chart of the method is presented in FIG. 7. It should be noted also that, in this case, the blunting step is also not necessary because the preliminary RT-PCR steps generates polynucleotide species with blunt ends. In addition, the adapter ligation is also not necessary for conducting other rounds of enrichment because the same primers used in the preliminary RT-PCT step may be used for other rounds of enrichment.

Example 5

Identification of Sequence Differences Between the Genomes of Two Strains of a Given Pathogen that Differ in Their Sensitivity to a Given Drug The following protocol provides for the identification of sequence differences between the genomes of two strains of a given bacterial pathogen that differ in their sensitivity to a given antibiotic.

The genomic DNA from both strains are isolated using techniques well known in the art (see Current Protocol in Molecular Biology, Volume 1, Chapter 2.4, supra). Then, 2 to 5 micrograms of the genomic DNA of the first strain is mixed with an equal amount of the genomic DNA of the second strain. The resulting DNA mixture is divided in 3 tubes. Then, each of the 3 DNA mixtures is digested with a different 6-base cutter restriction endonuclease, for example EcoRV, PvuII and DraI, so that the average size of the DNA molecules in each mixture is reduced to about 4 to 5 Kb. Conditions for digesting DNA molecules with restriction endonucleases are well known to those skilled in the art. Usually, 1 or 2 micrograms of DNA are digested with 2 to 5 units of restriction endonuclease in a total reaction volume of 50 microliters during one hour at 37 degree Celsius using the appropriate buffer provide by the supplier. The reason why three different reduction patterns are used is to reduce the probability that cuts are generated within a nucleic acid difference, thus precluding the identification of said nucleic acid difference. Performing fragmentation by different means, here three different restriction enzymes, thus increases the probability that each nucleic acid difference will be left intact by the reduction step and subsequently identified. Let $M0_{EcoRV}$, $M0_{PvuII}$ and $M0_{DraI}$ be the resulting 3 DNA mixtures obtained after digestion.

Then, the essentially same procedure as described in Example 2 is carried out on those 3 mixtures to obtain 3 new mixtures enriched in DNA fragments associated with the sequence differences existing between the two strains. Briefly, the DNA fragments of the $M0_{EcoRV}$, $M0_{PvuII}$ and $M0_{DraI}$ mixtures are denatured, then renatured. If one of the strain differs from the other by either one or several deletions or one or several insertions, duplex polynucleotides harboring internal single-stranded region(s) can form when a strand from one strain representing a region associated with a sequence difference will anneal to a complementary strand from the other strain. The 3 samples obtained after the renaturation step ($M0'_{EcoRV}$, $M0'_{PvuII}$ and $M0'_{DraI}$) are next submitted to the cleaning, blunting and adapter ligation steps. The resulting mixtures are now called $M0'''_{EcoRV}$, $M0'''_{PvuII}$ and $M0'''_{DraI}$. ISSRHs within these 3 mixtures are then selected using the single-stranded trap of the invention. Preferably, a BNDC column is used as the RE for the SST. $M0'_{EcoRV}$, $M0'_{PvuII}$ and $M0'_{DraI}$ are adjusted to 1M NaCl and then mixed with 100 mg of BNDC previously equilibrated with 50 mM Tris-HCl pH 8, 1 M NaCl. The mixture is agitated for 1 to 4 hours at room temperature. Then, the BNDC is pelleted at 14,000 rpm for 3 minutes and the supernatant is discarded because at high salt concentrations, BNDC is able to retain single stranded DNA but not double stranded DNA. Then, the BNDC is washed two to three times with a 50 mM Tris-HCl pH 8, 1 M NaCl buffer. For each wash, the BNDC is first resuspended and maintained in suspension for 2 to 5 minutes, pelleted by centrifugation, and then the supernatant is discarded. The polynucleotides that bound BNDC, mostly ISSRHs, are recovered by resuspending the washed BNDC in 500 microliters of an elution buffer (50% formamide, 10 mM Tris-HCl pH 8, 1 M NaCl) and maintaining the BNDC in suspension for 5 minutes, then pelleting the BNDC by centrifugation for 5 minutes and recovering the supernatant. The recovered polynucleotides are then ethanol precipitated.

After PCR amplification of the 3 mixtures selected by the single-stranded trap, polynucleotides containing the sequence differences are either directly cloned or submitted to another round of enrichment. At the end of the process, 3 libraries enriched in DNA fragments harboring sequence differences between the two strains are obtained (NAD-Li). These sequence differences can be characterized by sequencing the library or by any method known to the one skilled in the art.

Example 6

Figure 8:
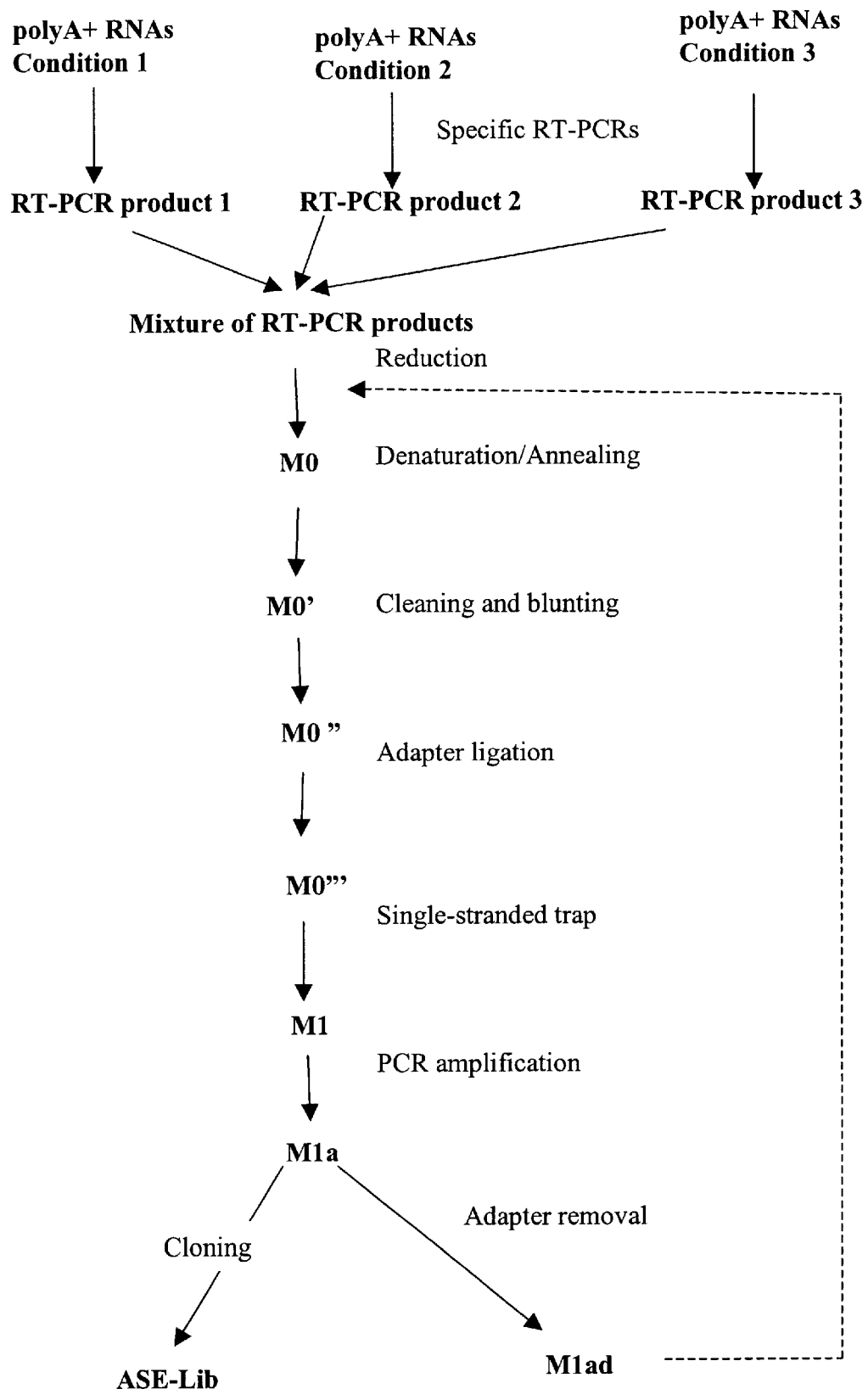
FIG. 8 is a flow chart illustrating several steps of a method for obtaining a library enriched with alternative splicing events for a single gene or limited set of genes and for several physiological conditions (ASE-Lib). The dashed line illustrates the enrichment loop that may be reiterated several times if necessary. More information on this method is disclosed in Example 6.

Isolation and Identification of Alternative Splicing Events for a Single Gene in Several Conditions This method, as illustrated in FIG. 8, allows to obtain a cDNA library enriched in alternative splicing events characteristic of differences between several sources, environments or physiological conditions.

This method contains the same steps as described in Example 3 with the difference that the cDNA sample on which the enrichment method is performed does not derive from a single source but from different cDNA samples that are mixed together.

Briefly, several targeted cDNA samples are prepared for gene X from initial samples deriving from different sources, environments, or physiological conditions. Then, equal amounts of these targeted cDNA samples are mixed together in order to constitute the polynucleotide sample on which the enrichment procedure is performed.

Then, ASE identification is carried out using the same procedure as described in Example 3. However, in order to determine whether the identified ASE originate from the presence of alternative splicing isoforms within one or more of the cDNA samples used to obtain the mixed polynucleotide sample (intra sample difference), or from the presence of different alternative splicing isoforms in different cDNA samples (inter sample difference), polynucleotides originating from the mixed polynucleotide sample is spotted in parallel with polynucleotides originating from each polynucleotide sample individually. Thus, an ASE identified in the mixed sample and also in one or several initial polynucleotide samples will result from intra sample differences whereas an ASE identified solely on the mixed sample and on none of the initial cDNA samples will result from inter sample difference.

Example 7

Figure 9:
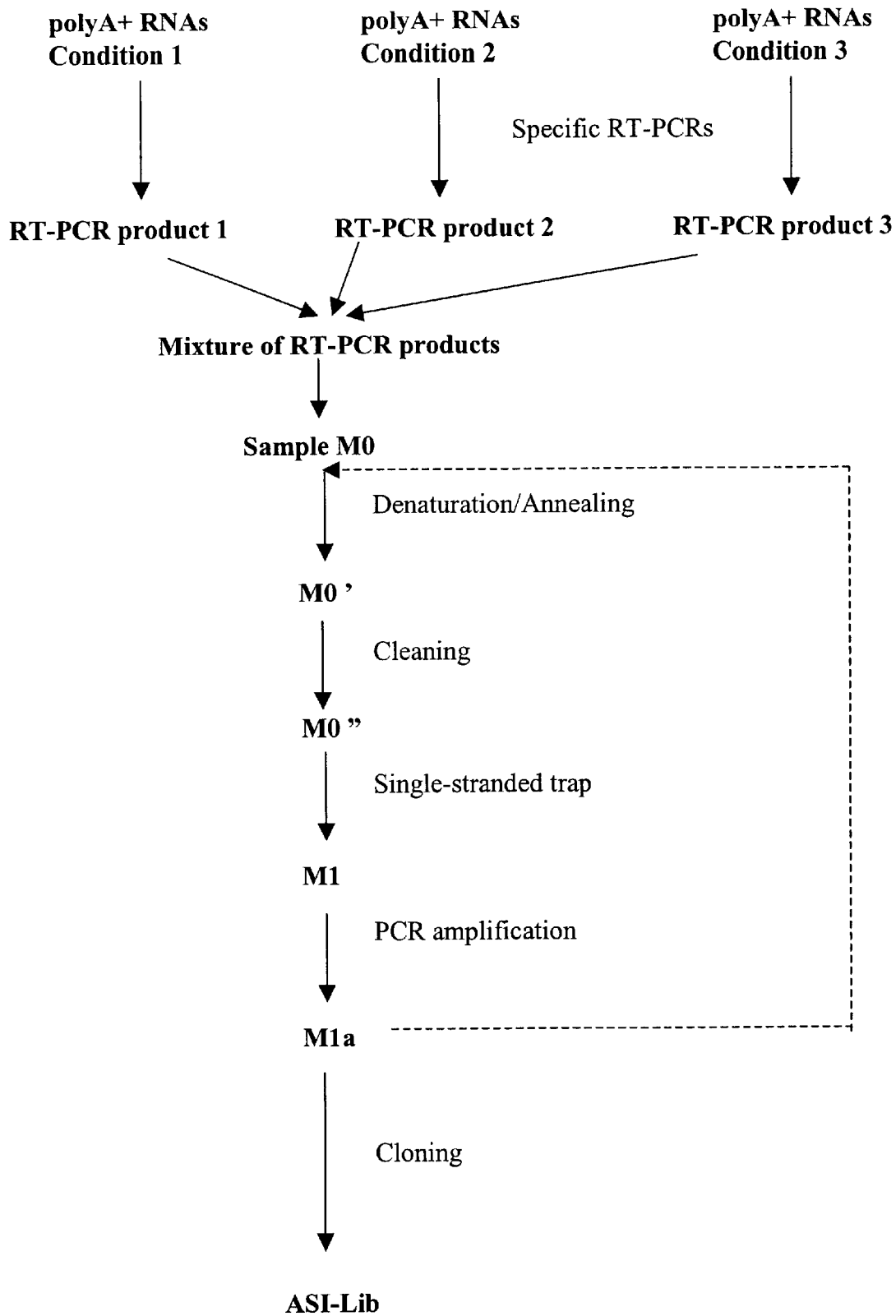
FIG. 9 is a flow chart illustrating several steps of the method for obtaining a library of isoforms for a single gene or limited set of genes and for several physiological conditions (ASI-Lib). The dashed line illustrates the enrichment loop that may be reiterated several times if necessary. More information on this method is disclosed in Example 7.

Isolation and Identification of Alternative Splicing Isoforms for a Single Gene in Several Conditions This method, as illustrated in FIG. 9, allows to obtain libraries of cDNA isoforms for a single gene or limited set of genes for several physiological conditions. The same procedure as described in Example 4 is used except that the cDNA sample on which the enrichment method is performed does not derive from a single source but from different cDNA samples that are mixed together as described in Example 6.

The present invention has been described with reference to certain preferred embodiments. Various modifications and alteration the above-described procedures that do not depart from the spirit and scope of the present invention will be apparent to one ordinary skilled in the art and are intended to be encompassed within the following claims.

Sequence Listing Free Text

Sequence source:/note="synthetic construct"

What is claimed:

1. A method of isolating or selecting related DNA molecules harboring nucleic acid differences in a DNA sample, said method comprising the selection of heteroduplexes containing at least one internal single stranded region with a single stranded trap, wherein
   i) said heteroduplexes are formed between said related DNA molecules,
   ii) said internal single stranded regions represent said nucleic acid differences, and
   iii) the single stranded trap involves the use of a Recognition Element having preferential affinity for single-stranded DNA compared to double stranded DNA that is a single strand binding protein.

2. A method of isolating or selecting related DNA harboring nucleic acid differences in a DNA sample, comprising the following steps:
   (a) obtaining a DNA sample containing said related DNA molecules;
   (b) denaturing DNA molecules present in said sample;
   (c) annealing said denatured DNA molecules to allow the formation of heteroduplexes between said related DNA molecules harboring nucleic acid differences; and,
   (d) isolating or selecting heteroduplexes containing at least one internal single stranded region using a single-stranded trap comprising a Recognition Element that is a single strand DNA binding protein.

3. The method of claim 2, wherein said method comprises the step of reducing the size of DNA molecules.

4. The method of claim 2, wherein said method comprises the steps of:
   i) removing single stranded regions other than internal single stranded regions on heteroduplexes containing at least one internal single stranded region by cleaning and blunting DNA molecules obtained after step (c); and, optionally,
   ii) ligating adapters to the ends of said heteroduplexes, wherein said steps are performed before step (d).

5. The method of claim 2, wherein said method comprises a step of amplifying said isolated or selected heteroduplexes.

6. The method of claim 1, wherein said DNA sample comprises DNA molecules from a single source, a single environment or a single physiological condition.

7. The method of claim 1, wherein said DNA sample comprises a mixture of DNA molecules from at least two different sources, two different environments or two different physiological conditions.

8. The method of claim 1, wherein said DNA sample comprises cDNA.

9. The method of claim 1, wherein said DNA sample comprises DNA molecules derived from a single gene or a limited set of genes.

10. The method of claim 1, wherein said method comprises the following steps:
    i) mixing said sample with said Recognition Element under condition to allow (a) the binding of said internal single stranded regions within said heteroduplexes to said Recognition Element and (b) subsequent formation of internal single stranded region containing heteroduplex-recognition element complexes; and
    ii) separating said complexes from said sample.

11. The method of claim 2, wherein step (d) of said method comprises the following steps:
    (i) immobilizing said Recognition Elements;
    (ii) bringing said immobilized Recognition Elements into contact with said annealed sample to allow
       (a) the binding of said internal single stranded regions within said heteroduplexes to said Recognition Elements and (b) subsequent formation of internal single stranded region containing heteroduplex-recognition element complexes; and
    (iii) removing the unbound DNAs.

12. The method of claim 1, wherein said Recognition Element is a Single Strand Binding Protein selected from the group consisting of *E Coli*. SSB, the product of gene 32 of phage T4, adenovirus DBP and calf thymus UP1.

13. The method of claim 1, wherein said nucleic acid difference comprises an insertion, deletion, or replacement of at least 15 nucleotides.

14. The method of claim 2, wherein said DNA sample comprises DNA molecules from a single source, a single environment or a single physiological condition.

15. The method of claim 2, wherein said DNA sample comprises a mixture of DNA molecules from at least two different sources, environments or physiological conditions.

16. The method of claim 2, wherein said DNA sample comprises cDNA.

17. The method of claim 2, wherein said DNA sample comprises DNA molecules derived from a single gene or a limited set of genes.

18. The method of claim 2, wherein said Recognition Element is a single strand binding protein selected from the group consisting of *E. Coli* SSB, the product of gene 32 of phage T4, adenovirus DPB and calf thymus UP1.

19. The method of claim 2, wherein said nucleic acid difference comprises an insertion, deletion, or replacement of at least 15 nucleotides.

20. The method of claim 2 wherein step (d) of said method is repeated more than one time on the same sample.

21. The method of claim 2 wherein said method comprises an additional step of recovering said related DNA from internal single stranded region containing heteroduplex-recognition element complexes.

22. The method of claim 2 wherein said method comprises a step of cloning said DNA harboring nucleic acid differences.

23. The method of claim 2 wherein said method comprises a step of sequencing said DNA harboring nucleic acid differences.

* * * * *

UNITED STATES PATENT AND TRADEMARK OFFICE
CERTIFICATE OF CORRECTION

PATENT NO. : 6,632,610 B2
DATED : October 14, 2003
INVENTOR(S) : Gilbert Pierre Thill It is certified that error appears in the above-identified patent and that said Letters Patent is hereby corrected as shown below:

Title page,
Item [73], Assignee, name "Gensat S.A." should read -- Genset, S.A. --.

Column 6,
Line 5, "sample. Alternatively, said" should read -- sample
                                                 Alternatively, said --.

Column 36,
Line 17, "fornamide" should read -- formamide --.

Column 47,
Line 12, "5'OH-CCCGCCACGTCCAAGCGGCCGCAG-"
should read
-- 5'OH-CCCGCCACGTCCAAGCGGCCGCAG- --.
Line 15, "CTGCGGCCGCTTGGACGTGGCG-"
should read -- CTGCGGCCGCTTGGACGTGGCG- --.
Line 33, "Tran" should read -- trap --.

Column 48,
Line 37, "molecules of M1 a are" should read -- molecules of M1a are --.

Column 52,
Line 8, "and $M0_{DraI}$)" should read -- and $M0'_{DraI}$) --.

UNITED STATES PATENT AND TRADEMARK OFFICE
CERTIFICATE OF CORRECTION

PATENT NO. : 6,632,610 B2
DATED : October 14, 2003
INVENTOR(S) : Gilbert Pierre Thill It is certified that error appears in the above-identified patent and that said Letters Patent is hereby corrected as shown below:

<u>Column 54,</u>
Line 47, "the selection of" should read -- the selection or isolation of --.
Lines 54-56, "Element having preferential affinity for single-stranded DNA compared to double stranded DNA that is a single strand binding protein" should read
-- Element that is a single strand binding protein having preferential affinity for single-stranded DNA compared to double stranded DNA --.

Signed and Sealed this

Twenty-seventh Day of January, 2004

JON W. DUDAS
*Acting Director of the United States Patent and Trademark Office*

UNITED STATES PATENT AND TRADEMARK OFFICE
CERTIFICATE OF CORRECTION

PATENT NO. : 6,632,610 B2
DATED : October 14, 2003
INVENTOR(S) : Gilbert Pierre Thill It is certified that error appears in the above-identified patent and that said Letters Patent is hereby corrected as shown below:

Title page,
Item [73], Assignee, name "Gensat S.A." should read -- Genset, S.A. --.

Column 6,
Line 5, "sample. Alternatively, said" should read -- sample.
                                                                              Alternatively, said --.

Column 36,
Line 17, "fornamide" should read -- formamide --.

Column 47,
Line 12, "5'OH-CCCGCCACGTCCAAGCGGCCGCAG-"
should read
-- 5'OH-CCCGCCACGTCCAAGCGGCCGCAG- --.
Line 15, "CTGCGGCCGCTTGGACGTGGCG-"
should read -- CTGCGGCCGCTTGGACGTGGCG- --.
Line 33, "Tran" should read -- trap --.

Column 48,
Line 37, "molecules of M1 a are" should read -- molecules of M1a are --.

Column 52,
Line 8, "and M0$_{DraI}$)" should read -- and M0'$_{DraI}$) --.

UNITED STATES PATENT AND TRADEMARK OFFICE
CERTIFICATE OF CORRECTION

PATENT NO. : 6,632,610 B2
DATED : October 14, 2003
INVENTOR(S) : Gilbert Pierre Thill It is certified that error appears in the above-identified patent and that said Letters Patent is hereby corrected as shown below:

Column 54,
Line 47, "the selection of" should read -- the selection or isolation of --.
Lines 54-56, "Element having preferential affinity for single-stranded DNA compared to double stranded DNA that is a single strand binding protein" should read
-- Element that is a single strand binding protein having preferential affinity for single-stranded DNA compared to double stranded DNA --.

This certificate supersedes Certificate of Correction issued January 27, 2004.

Signed and Sealed this

Second Day of March, 2004

JON W. DUDAS
*Acting Director of the United States Patent and Trademark Office*